(12) United States Patent
During

(10) Patent No.: US 11,761,006 B2
(45) Date of Patent: Sep. 19, 2023

(54) USE OF MIR101 OR MIR128 IN THE TREATMENT OF SEIZURE DISORDERS

(71) Applicant: Ovid Therapeutics Inc., New York, NY (US)

(72) Inventor: Matthew During, Weston, CT (US)

(73) Assignee: Ovid Therapeutics Inc., New York, NY (US)

( * ) Notice: Subject to any disclaimer, the term of this patent is extended or adjusted under 35 U.S.C. 154(b) by 0 days.

(21) Appl. No.: 16/950,395

(22) Filed: Nov. 17, 2020

(65) Prior Publication Data

US 2021/0095292 A1 Apr. 1, 2021

Related U.S. Application Data

(63) Continuation of application No. 16/211,309, filed on Dec. 6, 2018, now Pat. No. 10,870,855.

(Continued)

(51) Int. Cl.
*C12N 15/113* (2010.01)
*A61K 35/761* (2015.01)
(Continued)

(52) U.S. Cl.
CPC ........ *C12N 15/1137* (2013.01); *A61K 9/0085* (2013.01); *A61K 9/127* (2013.01);
(Continued)

(58) Field of Classification Search
CPC .............. C12N 15/113; C12N 15/1137; C12N 2310/141; C12N 2320/32; A61K 35/761
See application file for complete search history.

(56) References Cited

U.S. PATENT DOCUMENTS

| 3,499,437 A | 3/1970 | Balamuth |
| 4,303,636 A | 12/1981 | Gordon |

(Continued)

FOREIGN PATENT DOCUMENTS

| WO | 2014096418 A2 | 6/2014 |
| WO | 2016073704 A1 | 5/2016 |

(Continued)

OTHER PUBLICATIONS

Tan et al. (Science, 2013 vol. 342:1254-1258) (Supplementary Information/Materials).*

(Continued)

*Primary Examiner* — Terra C Gibbs
(74) *Attorney, Agent, or Firm* — Carter, DeLuca and Farrell LLP

(57) ABSTRACT

Methods of treating a seizure disorder in a patient in need thereof are provided which include delivering to the patient an effective amount of a composition that increases the level of microRNA-101 molecules in brain cells of the patient. Methods of treating a seizure disorder in a patient in need thereof are provided which include delivering to the patient an effective amount of a composition that increases the level of microRNA-128 molecules in brain cells of the patient. Methods of treating a seizure disorder in a patient in need thereof are provided which include administering a vector encoding microRNA-101, pri-miR101 or pre-miR101 to the patient. Methods of treating a seizure disorder in a patient in need thereof are provided which include administering a vector encoding microRNA-128, pri-miR128 or pre-miR128 to the patient. In embodiments, increased levels of microRNA-101 and/or microRNA-128 cause improvement in one or more symptoms of the seizure disorder.

16 Claims, 14 Drawing Sheets

Specification includes a Sequence Listing.

Related U.S. Application Data

(60) Provisional application No. 62/595,255, filed on Dec. 6, 2017.

(51) Int. Cl.
  A61K 9/127 (2006.01)
  A61K 9/00 (2006.01)
  A61P 25/08 (2006.01)

(52) U.S. Cl.
  CPC ............ *A61K 35/761* (2013.01); *A61P 25/08* (2018.01); *C12N 15/113* (2013.01); *A61K 9/0019* (2013.01); *C12N 2310/141* (2013.01); *C12N 2320/32* (2013.01); *C12N 2330/51* (2013.01)

(56) References Cited

U.S. PATENT DOCUMENTS

| | | | |
|---|---|---|---|
| 4,315,514 | A | 2/1982 | Drewes et al. |
| 4,923,437 | A | 5/1990 | Gordon |
| 5,059,415 | A | 10/1991 | Neuwelt |
| 5,112,596 | A | 5/1992 | Malfroy-Camine |
| 5,291,890 | A | 3/1994 | Cline et al. |
| 5,307,816 | A | 5/1994 | Hashimoto et al. |
| 5,368,032 | A | 11/1994 | Cline et al. |
| 5,438,989 | A | 8/1995 | Hochman et al. |
| 5,443,068 | A | 8/1995 | Cline et al. |
| 5,465,718 | A | 11/1995 | Hochman et al. |
| 5,485,839 | A | 1/1996 | Aida et al. |
| 5,524,620 | A | 6/1996 | Rosenschein |
| 5,526,814 | A | 6/1996 | Cline et al. |
| 5,752,515 | A | 5/1998 | Jolesz et al. |
| 10,870,855 | B2 | 12/2020 | During |
| 2009/0005711 | A1 | 1/2009 | Konofagou et al. |

FOREIGN PATENT DOCUMENTS

| | | |
|---|---|---|
| WO | 2017137585 A1 | 8/2017 |
| WO | 2018170223 A1 | 9/2018 |

OTHER PUBLICATIONS

Meena Azzollini (updated on May 31, 2021 and downloaded from Cortical Dysplasia: Symptoms, Causes, Diagnosis, Treatment, Coping (verywellfamily.com)).*

Focal cortical dysplasia from Wikipedia (downloaded on Jun. 8, 2022 from Focal cortical dysplasia—Wikipedia).*

McSweeney et al. (Genome Research, (Aug. 2016 vol. 26:1411-1416, plus Supplementary Information).*

Charbel et al., "Assessment of Tropism and Effectiveness of New Primate-Derived Hybrid Recombinant AAV Serotypes in the Mouse and Primate Retina," PLOS One, vol. 8, Issur 4, Apr. 2013; e60361; 12 pages.

Lippi et al., "MicroRNA-101 Regulates Multiple Developmental Programs to Constrain Excitation in Adult Neural Networks," Neuron 2016, vol. 92, No. 6; pp. 1337-1351.

Joanna Kabat, Focal cortical dysplasia—review, Polish Journal of Radiology, 2012, vol. 77, No. 2; pp. 35-43.

International Search Report and Written Opinion of the International Searching Authority, dated Apr. 9, 2019, corresponding to counterpart corresponding International Application No. PCT/US18/64158; 18 total pages.

European Search Report dated Nov. 8, 2020, corresponding to counterpart European Application No. 18886725.3; 7 pages.

Epileptogenesis—Wikipedia downloaded on Mar. 18, 2020 from https://en.wikipedia.org/wiki/Epileptogenesis.

Franich et al., "AAV vector-mediated RNAi of Mutant Huntingtin Expression is Neuroprotective in a Novel Genetic Rat Model of Hintington's Disease," Mol. Ther., May 2008, vol. 16, No. 5; pp. 947-956.

Liu et al., "Ultrasound-Enhanced Drug Transport and Distribution in the Brain," AAPS PharmaSciTech, Sep. 2010, vol. 11, No. 3; Research Article, pp. 1005-1017.

Powell, Ph.D., et al., "Viral Expression Cassette Elements to Enhance Transgene Target Specificity and Expression in Gene Therapy," Discover Med., Jan. 2015, vol. 19, No. 102; pp. 49-57.

Blume et al., ILAE Commission Report, "Glossary of Descriptive Terminology for Ictal Semiology; Report of the ILAE Task Force on Classification Terminology," Epilepsia, (2001) vol. 42, No. 9; pp. 1212-1218.

Tolman et al., "Treatment options for refractory and difficult to treat seizures: focus on vigabatrin," Therapeutics and Clinical Risk Management, (2011), vol. 7; pp. 367-375.

Bremner et al., "The Chemistry of Ultrasonic Degradation of Organic Compounds,", Current Organic Chemistry, (2011), vol. 15, No. 2; pp. 168-177.

Hynynen et al., "Local and reversible blood-brain barrier disruption by noninvasive focused ultrasound at frequencies suitable for trans-skull sonications," NeuroImage 24 (2005); pp. 12-20.

Varambally et al., "Genomic Loss of microRNA-101 Leads to Overexpression of Histone Methyltransferase EZH2 in cancer,", Science 2008, vol. 322, Dec. 12, 2008; pp. 1695-1699.

Huang et al., "MicroRNA-101 attenuates pulmonary fibrosis by inhibiting fibroblast proliferation and activation," Journal of Biological Chemistry, 2017, vol. 292, No. 40; pp. 16420-16439.

Tan et al., "MicroRNA-128 governs neuronal excitability and motor behavior in mice," Science, Dec. 6, 2013, vol. 342, No. 6163; pp. 1254-1258.

Li et al., "MicroRNAs Dysregulation in Epilepsy," ScienceDirect, Brain Research 1584, (2014); pp. 94-104.

Ryan et al, "Experimental Brain Hyperthermia: Techniques for Heat Delivery and Thermometry", Int J. Radiation Oncology Biol. Phys, vol. 20., pp. 739-750, 1991.

Le Bihan and Turner, "The Capillary Network: A Link between IVIM and Classical Perfusion", Magnetic Resonance in Medicine vol. 27, pp. 171-178, 1992.

Hills and James, "Microbubble Damage to the Blood-Brain Barrier: Relevance to Decompression Sickness", Undersea Biomedical Research, vol. 18, No. 2, pp. 111-116, 1991.

Polyashuk, "Permeability of Hemato-Encephasic Barrier Under the Effect of Supersonic Vibrations", Permeability of Hemato-Encephalic Barrier, p. 415 (parent abstract).

J.T. Patrick et al, "Focal Modification of the Blood-Brain Barrier with High Intensity Ultrasound: Experimental Results and Potential Application for Brain Tumor Therapy" Clinical Research, vol. 35, No. 1, 1987 (Parent abstract).

Mitragotri et al, "Ultrasound-Mediated Transdermal Protein Delivery" Science vol. 269, pp. 850-853, Aug. 11, 1993.

Vykhodtseva et al, "Histologic Effects of High Intensity Pulsed Ultrasound Exposure With Subharmonic Emission in Rabbit Brain In Vivo", Ultrasound in Med. & Biol. vol. 21, Not. 7, pp. 969-979, 1995.

J.T. Patrick et al, "Ultrasound and the Blood-Brain Barrier" In Consensus on Hyperthermia for the 1990s, Ed. H. I. Bicher et al, Plenum Press, New York 1990.

* cited by examiner pAM/CBA-miR101-1-WPRE-BGHpA

```
       1         10        20        30        40        50
       |         |         |         |         |         |
TAGCTGCGCGCTCGCTCGCTCACTGAGGCCGCCCGGGCAAAGCCCGGGCG
TCGGGCGACCTTTGGTCGCCCGGCCTCAGTGAGCGAGCGAGCGCGCAGAG
AGGGAGTGGCCAACTCCATCACTAGGGGTTCCTTGTAGTTAATGATTAAC
CCGCCATGCTACTTATCTACGTAGCCATGCTCTAGGTACCATTGACGTCA
ATAATGACGTATGTTCCCATAGTAACGCCAATAGGGACTTTCCATTGACG
TCAATGGGTGGAGTATTTACGGTAAACTGCCCACTTGGCAGTACATCAAG
TGTATCATATGCCAAGTACGCCCCCTATTGACGTCAATGACGGTAAATGG
CCCGCCTGGCATTATGCCCAGTACATGACCTTATGGGACTTTCCTACTTG
GCAGTACATCTACGTATTAGTCATCGCTATTACCATGGTCGAGGTGAGCC
CCACGTTCTGCTTCACTCTCCCCATCTCCCCCCCTCCCCACCCCCAATT
TTGTATTTATTTATTTTTAATTATTTTGTGCAGCGATGGGGGCGGGGGG
GGGGGGGGGGCGCGCGCCAGGCGGGGCGGGGCGGGGCGAGGGGCGGGGCG
GGGCGAGGCGGAGAGGTGCGGCGGCAGCCAATCAGAGCGGCGCGCTCCGA
AAGTTTCCTTTTATGGCGAGGCGGCGGCGGCGGCGGCCCTATAAAAGCG
AAGCGCGCGGCGGGCGGGAGTCGCTGCGCGCTGCCTTCGCCCCGTGCCCC
GCTCCGCCGCCGCCTCGCGCCGCCCGCCCCGGCTCTGACTGACCGCGTTA
CTCCCACAGGTGAGCGGGCGGGACGGCCCTTCTCCTCCGGGCTGTAATTA
GCGCTTGGTTTAATGACGGCTTGTTTCTTTTCTGTGGCTGCGTGAAAGCC
TTGAGGGGCTCCGGGAGGGCCCTTTGTGCGGGGGGAGCGGCTCGGGGCTG
TCCGCGGGGGACGGCTGCCTTCGGGGGGACGGGGCAGGGCGGGGTTCG
GCTTCTGGCGTGTGACCGGCGGCTCTAGAGCCTCTGCTAACCATGTTCAT
GCCTTCTTCTTTTCCTACAGCTCCTGGGCAACGTGCTGGTTATTGTGCT
GTCTCATCATTTTGGCAAAGAATTGGATCCACTCGAGTGGAGCTCGCGAC
TAGTCGATTCGAATTCGTCGACTGGATCCAGTACCGAGGAGATCTGCGCC
GCGATCGCTGCTGGAAGCTTACTGCATATTTGATGTATTAGAGTGAAAAC
CTAATCATGCAGTTGTTCATCCTCATTAATATGGATAAGTCATGTGTTCA
TCTTTCATTCTAATTTAATTCAACTGGGCCTTTTAATATTTCAGCCTCAC
CACTTGCTGGGCTCTGATCCTTCTTTTTCTTCTGCCTCCTCACGTCTCCA
ACCAGAAGGTGATCTTTTAGTCCTTCACTTCATGGGGAGCCTTCAGAGAG
AGTAATGCAGCCACCAGAAAGGATGCCGTTGACCGACACAGTGACTGACA
GGCTGCCCTGGCTCAGTTATCACAGTGCTGATGCTGTCTATTCTAAAGGT
ACAGTACTGTGATAACTGAAGGATGGCAGCCATCTTACCTTCCATCAGAG
```

FIG. 2A

```
GAGCCTCACCGTACCCAGGAAGAAAGAAGGTGAAAGAGGAATGTGAAACA
GGTGGCTGGGACCCAGAAACCCTCTTACCCTGCACCTCTGTCATACTTCT
CCCGGGGCATAGGGAGAGTTATTCTGCTTCTCTTTGCCTTGTTTTGTAAC
ATGGGGTAGTTGTTGGTGCAGCCATGTTGTGCTGAGTGAACATATATTAA
GATCTTTGGAACCTTTAGGAGACTGAAAATAGGTAAGTATGAATTAGTAT
TTCTGGAATGGTATTCAGAGAACTTCGACGCGTACGCGGCGCTCGAGCA
GAAACTCATCTCAGAAGAGGATCTGGCAGCAAATGATATCAAGCTTATCG
ATAATCAACCTCTGGATTACAAATTTGTGAAAGATTGACTGGTATTCTT
AACTATGTTGCTCCTTTTACGCTATGTGGATACGCTGCTTTAATGCCTTT
GTATCATGCTATTGCTTCCCGTATGGCTTTCATTTTCCTCCTTGTATA
AATCCTGGTTGCTGTCTCTTTATGAGGAGTTGTGGCCCGTTGTCAGGCAA
CGTGGCGTGGTGTGCACTGTGTTTGCTGACGCAACCCCACTGGTTGGGG
CATTGCCACCACCTGTCAGCTCCTTTCCGGGACTTTCGCTTTCCCCTCC
CTATTGCCACGGCGGAACTCATCGCCGCCTGCCTTGCCCGCTGCTGGACA
GGGGCTCGGCTGTTGGGCACTGACAATTCCGTGGTGTTGTCGGGAAATC
ATCGTCCTTTCCTTGGCTGCTCGCCTGTGTTGCCACCTGGATTCTGCGCG
GGACGTCCTTCTGCTACGTCCCTTCGGCCCTCAATCCAGCGGACCTTCCT
TCCCGCGGCCTGCTGCCGGCTCTGCGGCCTCTTCCGCGTCTTCGCCTTCG
CCCTCAGACGAGTCGGATCTCCCTTTGGGCCGCCTCCCCGCATCGATACC
GTCGACTCGCTGATCAGCCTCGACTGTGCCTTCTAGTTGCCAGCCATCTG
TTGTTTGCCCCTCCCCGTGCCTTCCTTGACCCTGGAAGGTGCCACTCCC
ACTGTCCTTTCCTAATAAAATGAGGAAATTGCATCGCATTGTCTGAGTAG
GTGTCATTCTATTCTGGGGGGTGGGGTGGGGCAGGACAGCAAGGGGGAGG
ATTGGGAAGACAATAGCAGGCATGCTGGGGATGCGGTGGGCTCTATGGCT
TCTGAGGCGGAAAGAACCAGCTGGGGCTCGACTAGAGCATGGCTACGTAG
ATAAGTAGCATGGCGGGTTAATCATTAACTACAAGGAACCCCTAGTGATG
GAGTTGGCCACTCCCTCTGCGCGCTCGCTCGCTCACTGAGGCCGGGCG
ACCAAAGGTCGCCCGACGCCCGGGCTTTGCCCGGCGGCCTCAGTGAGCG
AGCGAGCGCGCAGAGCTTTTTGCAAAAGCCTAGGCCTCCAAAAAGCCTC
CTCACTACTTCTGGAATAGCTCAGAGGCCGAGGCGGCCTCGGCCTCTGCA
TAAATAAAAAATTAGTCAGCCATGGGGCGGAGAATGGGCGGAACTGGG
CGGAGTTAGGGGCGGGATGGGCGGAGTTAGGGGCGGGACTATGGTTGCTG
ACTAATTGAGATGCATGCTTTGCATACTTCTGCCTGCTGGGGAGCCTGGG
GACTTTCCACACCTGGTTGCTGACTAATTGAGATGCATGCTTTGCATACT
TCTGCCTGCTGGGGAGCCTGGGGACTTTCCACACCCTAACTGACACACAT
TCCACAGCTGCATTAATGAATCGGCCAACGCGCGGGGAGAGGCGGTTTGC
```

FIG. 2B

```
GTATTGGGCGCTCTTCCGCTTCCTCGCTCACTGACTCGCTGCGCTCGGTC
GTTCGGCTGCGGCGAGCGGTATCAGCTCACTCAAAGGCGGTAATACGGTT
ATCCACAGAATCAGGGGATAACGCAGGAAAGAACATGTGAGCAAAAGGCC
AGCAAAAGGCCAGGAACCGTAAAAAGGCCGCGTTGCTGGCGTTTTCCAT
AGGCTCCGCCCCCTGACGAGCATCACAAAAATCGACGCTCAAGTCAGAG
GTGGCGAAACCCGACAGGACTATAAAGATACCAGGCGTTTCCCCTGGAA
GCTCCCTCGTGCGCTCTCCTGTTCCGACCCTGCCGCTTACCGGATACCTG
TCCGCCTTTCTCCCTTCGGGAAGCGTGGCGCTTTCTCATAGCTCACGCTG
TAGGTATCTCAGTTCGGTGTAGGTCGTTCGCTCCAAGCTGGGCTGTGTGC
ACGAACCCCCGTTCAGCCCGACCGCTGCGCCTTATCCGGTAACTATCGT
CTTGAGTCCAACCCGGTAAGACACGACTTATCGCCACTGGCAGCAGCCAC
TGGTAACAGGATTAGCAGAGCGAGGTATGTAGGCGGTGCTACAGAGTTCT
TGAAGTGGTGGCCTAACTACGGCTACACTAGAAGAACAGTATTTGGTATC
TGCGCTCTGCTGAAGCCAGTTACCTTCGGAAAAAGAGTTGGTAGCTCTTG
ATCCGGCAAACAAACCACCGCTGGTAGCGGTGGTTTTTTTGTTTGCAAGC
AGCAGATTACGCGCAGAAAAAAGGATCTCAAGAAGATCCTTTGATCTTT
TCTACGGGGTCTGACGCTCAGTGGAACGAAAACTCACGTTAAGGGATTTT
GGTCATGAGATTATCAAAAGGATCTTCACCTAGATCCTTTTAAATTAAA
AATGAAGTTTTAAATCAATCTAAAGTATATATGAGTAAACTTGGTCTGAC
AGTTACCAATGCTTAATCAGTGAGGCACCTATCTCAGCGATCTGTCTATT
TCGTTCATCCATAGTTGCCTGACTCCCCGTCGTGTAGATAACTACGATAC
GGGAGGGCTTACCATCTGGCCCCAGTGCTGCAATGATACCGCGAGACCCA
CGCTCACCGGCTCCAGATTTATCAGCAATAAACCAGCCAGCCGGAAGGGC
CGAGCGCAGAAGTGGTCCTGCAACTTTATCCGCCTCCATCCAGTCTATTA
ATTGTTGCCGGGAAGCTAGAGTAAGTAGTTCGCCAGTTAATAGTTTGCGC
AACGTTGTTGCCATTGCTACAGGCATCGTGGTGTCACGCTCGTCGTTTGG
TATGGCTTCATTCAGCTCCGGTTCCCAACGATCAAGGCGAGTTACATGAT
CCCCATGTTGTGCAAAAAGCGGTTAGCTCCTTCGGTCCTCCGATCGTT
GTCAGAAGTAAGTTGGCCGCAGTGTTATCACTCATGGTTATGGCAGCACT
GCATAATTCTCTTACTGTCATGCCATCCGTAAGATGCTTTTCTGTGACTG
GTGAGTACTCAACCAAGTCATTCTGAGAATAGTGTATGCGGCGACCGAGT
TGCTCTTGCCCGGCGTCAATACGGGATAATACCGCGCCACATAGCAGAAC
TTTAAAAGTGCTCATCATTGGAAAACGTTCTTCGGGGCGAAAACTCTCAA
GGATCTTACCGCTGTTGAGATCCAGTTCGATGTAACCCACTCGTGCACCC
AACTGATCTTCAGCATCTTTTACTTTCACCAGCGTTTCTGGGTGAGCAAA
AACAGGAAGGCAAAATGCCGCAAAAAAGGGAATAAGGGCGACACGGAAAT
```

FIG. 2C

```
GTTGAATACTCATACTCTTCCTTTTTCAATATTATTGAAGCATTTATCAG
GGTTATTGTCTCATGAGCGGATACATATTTGAATGTATTTAGAAAAATAA
ACAAATAGGGGTTCCGCGCACATTTCCCCGAAAAGTGCCACCTGACGTCT
AAGAAACCATTATTATCATGACATTAACCTATAAAAATAGGCGTATCACG
AGGCCCTTTCGTCTCGCGCGTTTCGGTGATGACGGTGAAAACCTCTGACA
CATGCAGCTCCCGGAGACGGTCACAGCTTGTCTGTAAGCGGATGCCGGGA
GCAGACAAGCCCGTCAGGGCGCGTCAGCGGGTGTTGGCGGGTGTCGGGGC
TGGCTTAACTATGCGGCATCAGAGCAGATTGTACTGAGAGTGCACCATTC
GACGCTCTCCCTTATGCGACTCCTGCATTAGGAAGCAGCCCAGTAGTAGG
TTGAGGCCGTTGAGCACCGCCGCCGCAAGGAATGGTGCATGCAAGGAGAT
GGCGCCCAACAGTCCCCGGCCACGGGGCCTGCCACCATACCCACGCCGA
ACAAGCGCTCATGAGCCCGAAGTGGCGAGCCCGATCTTCCCCATCGGTG
ATGTCGGCGATATAGGCGCCAGCAACCGCACCTGTGGCGCCGGTGATGCC
GGCCACGATGCGTCCGGCGTAGAGGATCTGGCTAGCGATGACCCTGCTGA
TTGGTTCGCTGACCATTTCCGGGTGCGGGACGGCGTTACCAGAAACTCAG
AAGGTTCGTCCAACCAAACCGACTCTGACGGCAGTTTACGAGAGAGATGA
TAGGGTCTGCTTCAGTAAGCCAGATGCTACACAATTAGGCTTGTACATAT
TGTCGTTAGAACGCGGCTACAATTAATACATAACCTTATGTATCATACAC
ATACGATTTAGGTGACACTATAGAATACACGGAATTAATTC
```

FIG. 2D pAM/CBA-miR128-2-WPRE-BGHpA

```
1         10        20        30        40        50
|         |         |         |         |         |
TAGCTGCGCGCTCGCTCGCTCACTGAGGCCGCCCGGGCAAAGCCCGGGCG
TCGGGCGACCTTTGGTCGCCCGGCCTCAGTGAGCGAGCGAGCGCGCAGAG
AGGGAGTGGCCAACTCCATCACTAGGGGTTCCTTGTAGTTAATGATTAAC
CCGCCATGCTACTTATCTACGTAGCCATGCTCTAGGTACCATTGACGTCA
ATAATGACGTATGTTCCCATAGTAACGCCAATAGGGACTTTCCATTGACG
TCAATGGGTGGAGTATTTACGGTAAACTGCCCACTTGGCAGTACATCAAG
TGTATCATATGCCAAGTACGCCCCTATTGACGTCAATGACGGTAAATGG
CCCGCCTGGCATTATGCCCAGTACATGACCTTATGGGACTTTCCTACTTG
GCAGTACATCTACGTATTAGTCATCGCTATTACCATGGTCGAGGTGAGCC
CCACGTTCTGCTTCACTCTCCCCATCTCCCCCCCTCCCCACCCCAATT
TTGTATTTATTTATTTTTAATTATTTTGTGCAGCGATGGGGGCGGGGGG
GGGGGGGGGGCGCGCCAGGCGGGGCGGGGCGGGGCGAGGGGCGGGGCG
GGGCGAGGCGGAGAGGTGCGGCGGCAGCCAATCAGAGCGGCGCGCTCCGA
AAGTTTCCTTTTATGGCGAGGCGGCGGCGGCGGCGGCCCTATAAAAGCG
AAGCGCGCGGCGGGCGGGAGTCGCTGCGCGCTGCCTTCGCCCCGTGCCCC
GCTCCGCCGCCGCCTCGCGCCGCCCGCCCCGGCTCTGACTGACCGCGTTA
CTCCCACAGGTGAGCGGGCGGGACGGCCCTTCTCCTCCGGGCTGTAATTA
GCGCTTGGTTTAATGACGGCTTGTTTCTTTTCTGTGGCTGCGTGAAAGCC
TTGAGGGGCTCCGGGAGGGCCCTTTGTGCGGGGGGAGCGGCTCGGGGCTG
TCCGCGGGGGGACGGCTGCCTTCGGGGGGGACGGGGCAGGGCGGGGTTCG
GCTTCTGGCGTGTGACCGGCGGCTCTAGAGCCTCTGCTAACCATGTTCAT
GCCTTCTTCTTTTTCCTACAGCTCCTGGGCAACGTGCTGGTTATTGTGCT
GTCTCATCATTTTGGCAAAGAATTGGATCCACTCGAGTGGAGCTCGCGAC
TAGTCGATTCGAATTCGTCGACTGGATCCAGTACCGAGGAGATCTGCGCC
GCGATCGCGTCTCCATAAATTATTTTTGATCCTTCTTCTGTTAAAGCAG
AAAGTCAACCATGTCCGTACCTTTCTAGTTCATACCTTCTTTTAATTTTT
TTTTTCTTTTCAATTTGAAGAGAGTGCTTCCTCTGTTCTTAAGGCTAGGG
AACCAAATTAGGTTGTTTCAATATCGTGCTAAAGATACTGCCTTTAGAA
GAAGGCTATTGACAATCCAGCGTGTCTCGGTGGAACTCTGACTCCATGGT
TCACTTTCATGATGGCCACATGCCTCCTGCCCAGAGCCCGGCAGCCACTG
TGCAGTGGGAAGGGGGCCGATACACTGTACGAGAGTGAGTAGCAGGTCT
CACAGTGAACCGGTCTCTTTCCCTACTGTGTCACACTCCTAATGGAATGC
CGTTATCCAAAGAGCAGCACGAACCCGACAGGGCTGAGTGGCTTGTGCTA
```

FIG. 6A

```
GGGAGAGGTTTGTGTCATTCCTGCTGACCAAACTGCAGGAAAAACTGCTA
ATTGTCATGCTGAAGACTGCCTGACGGGGAGACTCTGCCTTCTGTAAGTA
GGTCATGTAAAGAGCACGTGCTCCTTGCTGCTACTCATAGATGCCTGCTC
CGTGATCTGATTTCTGCACTGAATCTATGTTATGCATATGGAATGTATAC
AGATACATGTACGCGTACGCGGCCGCTCGAGCAGAAACTCATCTCAGAAG
AGGATCTGGCAGCAAATGATATCAAGCTTATCGATAATCAACCTCTGGAT
TACAAAATTTGTGAAGATTGACTGGTATTCTTAACTATGTTGCTCCTTT
TACGCTATGTGGATACGCTGCTTAATGCCTTTGTATCATGCTATTGCTT
CCCGTATGGCTTTCATTTTCTCCTCCTTGTATAAATCCTGGTTGCTGTCT
CTTTATGAGGAGTTGTGGCCCGTTGTCAGGCAACGTGGCGTGGTGTGCAC
TGTGTTTGCTGACGCAACCCCACTGGTTGGGGCATTGCCACCACCTGTC
AGCTCCTTTCCGGGACTTTCGCTTTCCCCTCCCTATTGCCACGGCGGAA
CTCATCGCCGCCTGCCTTGCCCGCTGCTGGACAGGGGCTCGGCTGTTGGG
CACTGACAATTCCGTGGTGTTGTCGGGAAATCATCGTCCTTTCCTTGGC
TGCTCGCCTGTGTTGCCACCTGGATTCTGCGCGGGACGTCCTTCTGCTAC
GTCCCTTCGGCCCTCAATCCAGCGGACCTTCCTTCCCGCGGCCTGCTGCC
GGCTCTGCGGCCTCTTCCGCGTCTTCGCCTTCGCCCTCAGACGAGTCGGA
TCTCCCTTTGGGCCGCCTCCCCGCATCGATACCGTCGACTCGCTGATCAG
CCTCGACTGTGCCTTCTAGTTGCCAGCCATCTGTTGTTTGCCCCTCCCCC
GTGCCTTCCTTGACCCTGGAAGGTGCCACTCCCACTGTCCTTTCCTAATA
AAATGAGGAAATTGCATCGCATTGTCTGAGTAGGTGTCATTCTATTCTGG
GGGGTGGGGTGGGCAGGACAGCAAGGGGGAGGATTGGGAAGACAATAGC
AGGCATGCTGGGGATGCGGTGGGCTCTATGGCTTCTGAGGCGGAAAGAAC
CAGCTGGGGCTCGACTAGAGCATGGCTACGTAGATAAGTAGCATGGCGGG
TTAATCATTAACTACAAGGAACCCCTAGTGATGGAGTTGGCCACTCCCTC
TCTGCGCGCTCGCTCGCTCACTGAGGCCGGGCGACCAAAGGTCGCCCGAC
GCCCGGGCTTTGCCCGGGCGGCCTCAGTGAGCGAGCGAGCGCGCAGAGCT
TTTTGCAAAAGCCTAGGCCTCCAAAAAAGCCTCCTCACTACTTCTGGAAT
AGCTCAGAGGCCGAGGCGGCCTCGGCCTCTGCATAAATAAAAAAAATTAG
TCAGCCATGGGGCGGAGAATGGGCGGAACTGGGCGGAGTTAGGGGCGGGA
TGGGCGGAGTTAGGGGCGGGACTATGGTTGCTGACTAATTGAGATGCATG
CTTTGCATACTTCTGCCTGCTGGGGAGCCTGGGGACTTTCCACACCTGGT
TGCTGACTAATTGAGATGCATGCTTTGCATACTTCTGCCTGCTGGGGAGC
CTGGGGACTTTCCACACCCTAACTGACACACATTCCACAGCTGCATTAAT
GAATCGGCCAACGCGCGGGGAGAGGCGGTTTGCGTATTGGGCGCTCTTCC
GCTTCCTCGCTCACTGACTCGCTGCGCTCGGTCGTTCGGCTGCGGCGAGC
```

FIG. 6B

```
GGTATCAGCTCACTCAAAGGCGGTAATACGGTTATCCACAGAATCAGGGG
ATAACGCAGGAAAGAACATGTGAGCAAAAGGCCAGCAAAAGGCCAGGAAC
CGTAAAAAGGCCGCGTTGCTGGCGTTTTCCATAGGCTCCGCCCCCTGA
CGAGCATCACAAAAATCGACGCTCAAGTCAGAGGTGGCGAAACCCGACAG
GACTATAAAGATACCAGGCGTTTCCCCTGGAAGCTCCCTCGTGCGCTCT
CCTGTTCCGACCCTGCCGCTTACCGGATACCTGTCCGCCTTTCTCCCTTC
GGGAAGCGTGGCGCTTTCTCATAGCTCACGCTGTAGGTATCTCAGTTCGG
TGTAGGTCGTTCGCTCCAAGCTGGGCTGTGTGCACGAACCCCCGTTCAG
CCCGACCGCTGCGCCTTATCCGGTAACTATCGTCTTGAGTCCAACCCGGT
AAGACACGACTTATCGCCACTGGCAGCAGCCACTGGTAACAGGATTAGCA
GAGCGAGGTATGTAGGCGGTGCTACAGAGTTCTTGAAGTGGTGGCCTAAC
TACGGCTACACTAGAAGAACAGTATTTGGTATCTGCGCTCTGCTGAAGCC
AGTTACCTTCGGAAAAAGAGTTGGTAGCTCTTGATCCGGCAAACAAACCA
CCGCTGGTAGCGGTGGTTTTTTTGTTTGCAAGCAGCAGATTACGCGCAGA
AAAAAAGGATCTCAAGAAGATCCTTTGATCTTTTCTACGGGGTCTGACGC
TCAGTGGAACGAAAACTCACGTTAAGGGATTTTGGTCATGAGATTATCAA
AAAGGATCTTCACCTAGATCCTTTTAAATTAAAAATGAAGTTTTAAATCA
ATCTAAAGTATATATGAGTAAACTTGGTCTGACAGTTACCAATGCTTAAT
CAGTGAGGCACCTATCTCAGCGATCTGTCTATTTCGTTCATCCATAGTTG
CCTGACTCCCCGTCGTGTAGATAACTACGATACGGGAGGGCTTACCATCT
GGCCCCAGTGCTGCAATGATACCGCGAGACCCACGCTCACCGGCTCCAGA
TTTATCAGCAATAAACCAGCCAGCCGGAAGGGCCGAGCGCAGAAGTGGTC
CTGCAACTTTATCCGCCTCCATCCAGTCTATTAATTGTTGCCGGGAAGCT
AGAGTAAGTAGTTCGCCAGTTAATAGTTTGCGCAACGTTGTTGCCATTGC
TACAGGCATCGTGGTGTCACGCTCGTCGTTTGGTATGGCTTCATTCAGCT
CCGGTTCCCAACGATCAAGGCGAGTTACATGATCCCCATGTTGTGCAAA
AAAGCGGTTAGCTCCTTCGGTCCTCCGATCGTTGTCAGAAGTAAGTTGGC
CGCAGTGTTATCACTCATGGTTATGGCAGCACTGCATAATTCTCTTACTG
TCATGCCATCCGTAAGATGCTTTTCTGTGACTGGTGAGTACTCAACCAAG
TCATTCTGAGAATAGTGTATGCGGCGACCGAGTTGCTCTTGCCCGGCGTC
AATACGGGATAATACCGCGCCACATAGCAGAACTTTAAAAGTGCTCATCA
TTGGAAAACGTTCTTCGGGGCGAAAACTCTCAAGGATCTTACCGCTGTTG
AGATCCAGTTCGATGTAACCCACTCGTGCACCCAACTGATCTTCAGCATC
TTTTACTTTCACCAGCGTTTCTGGGTGAGCAAAAACAGGAAGGCAAAATG
CCGCAAAAAAGGGAATAAGGGCGACACGGAAATGTTGAATACTCATACTC
TTCCTTTTTCAATATTATTGAAGCATTTATCAGGGTTATTGTCTCATGAG
```

FIG. 6C

```
CGGATACATATTTGAATGTATTTAGAAAAATAAACAAATAGGGGTTCCGC
GCACATTTCCCCGAAAAGTGCCACCTGACGTCTAAGAAACCATTATTATC
ATGACATTAACCTATAAAATAGGCGTATCACGAGGCCCTTTCGTCTCGC
GCGTTTCGGTGATGACGGTGAAAACCTCTGACACATGCAGCTCCGGAGA
CGGTCACAGCTTGTCTGTAAGCGGATGCCGGGAGCAGACAAGCCCGTCAG
GGCGCGTCAGCGGGTGTTGGCGGGTGTCGGGGCTGGCTTAACTATGCGGC
ATCAGAGCAGATTGTACTGAGAGTGCACCATTCGACGCTCTCCCTTATGC
GACTCCTGCATTAGGAAGCAGCCCAGTAGTAGGTTGAGGCCGTTGAGCAC
CGCCGCCGCAAGGAATGGTGCATGCAAGGAGATGGCGCCCAACAGTCCCC
CGGCCACGGGGCCTGCCACCATACCACGCCGAAACAAGCGCTCATGAGC
CCGAAGTGGCGAGCCCGATCTTCCCCATCGGTGATGTCGGCGATATAGGC
GCCAGCAACCGCACCTGTGGCGCCGGTGATGCCGGCCACGATGCGTCCGG
CGTAGAGGATCTGGCTAGCGATGACCCTGCTGATTGGTTCGCTGACCATT
TCCGGGTGCGGGACGGCGTTACCAGAAACTCAGAAGGTTCGTCCAACCAA
ACCGACTCTGACGGCAGTTTACGAGAGAGATGATAGGGTCTGCTTCAGTA
AGCCAGATGCTACACAATTAGGCTTGTACATATTGTCGTTAGAACGCGGC
TACAATTAATACATAACCTTATGTATCATACACATACGATTTAGGTGACA
CTATAGAATACACGGAATTAATTC
```

FIG. 6D

AAVRec3 Amino Acid Sequence

```
  1 MAADGYLPDW LEGNLSEGIR EWWDLKPGAP KPKANQQKQD DGRGLVLPGY RYLGPFNGLD
 61 KGEPVNEADA AALEHDKAYD QQLKAGDNPY LRYNHADAEF QERLQEDTSF GGNLGRAVFQ
121 AKKRVLEPLG LVEEAAKTAP GKKRPVEPSP QRSPDSSTGI GKKGQQPAKK RLNFGQTGDS
181 ESVPDPQPIG EPPAGPSGLG SGTMAAGGGA PMADNNEGAD GVGSSSGNWH CDSTWLGDRV
241 ITTSTRTWAL PTYNNHLYKQ ISNGTSGGST NDNTYFGYST PWGYFDFNRF HCHFSPRDWQ
301 RLINNNWGFR PKRLSFKLFN IQVKEVTQNE GTKTIANNLT STIQVFTDSE YQLPYVLGSA
361 HQGCLPPFPA DVFMIPQYGY LTLNNGSQAV GRSSFYCLEY FPSQMLRTGN NFEFSYTFED
421 VPFHSSYAHS QSLDRLMNPL IDQYLYYLSR TQSTGGTQGT QQLLFSQAGP ANMSAQAKNW
481 LPGPCYRQQR VSTTLSQNNN SNFAWTGATK YHLNGRDSLV NPGVAMATHK DDEERFFPSS
541 GVLMFGKQGA GRDNVDYSSV MLTSEEEIKT TNPVATEQYG VVADNLQQTN TGPIVGNVNS
601 QGALPGMVWQ NRDVYLQGPI WAKIPHTDGN FHPSPLMGGF GLKHPPPQIL IKNTPVPADP
661 PTTFNQSKLN SFITQYSTGQ VSVEIEWELQ KENSKRWNPE IQYTSNYYKS TSVDFAVNTE
721 GVYSEPRPIG TRYLTRNL
```

FIG. 8

SEQUENCE LISTING

```
<160> NUMBER OF SEQ ID NOS: 5

<210> SEQ ID NO 1
<211> LENGTH: 21
<212> TYPE: RNA
<213> ORGANISM: Homo sapiens
<220> FEATURE:
<221> NAME/KEY: misc_feature
<223> OTHER INFORMATION: mature sequence of human miR101

<400> SEQUENCE: 1
uacaguacug ugauaacuga a                                               21

<210> SEQ ID NO 2
<211> LENGTH: 23
<212> TYPE: RNA
<213> ORGANISM: Homo sapiens
<220> FEATURE:
<221> NAME/KEY: misc_feature
<223> OTHER INFORMATION: mature sequence of  miR128

<400> SEQUENCE: 2
gggggccgau acacuguacg aga                                             23

<210> SEQ ID NO 3
<211> LENGTH: 6141
<212> TYPE: DNA
<213> ORGANISM: Artificial Sequence
<220> FEATURE:
<223> OTHER INFORMATION: Synthetic construct: pAM/CBA-miR101-1-WPRE-
      BGHpA

<400> SEQUENCE: 3
tagctgcgcg ctcgctcgct cactgaggcc gcccgggcaa agcccgggcg tcgggcgacc         60
tttggtcgcc cggcctcagt gagcgagcga gcgcgcagag agggagtggc caactccatc        120 actagggggtt ccttgtagtt aatgattaac ccgccatgct acttatctac gtagccatgc        180
tctaggtacc attgacgtca ataatgacgt atgttcccat agtaacgcca atagggactt        240
tccattgacg tcaatgggtg gagtatttac ggtaaactgc ccacttggca gtacatcaag        300
tgtatcatat gccaagtacg ccccctattg acgtcaatga cggtaaatgg cccgcctggc        360
```

```
attatgccca gtacatgacc ttatgggact ttcctacttg gcagtacatc tacgtattag    420
tcatcgctat taccatggtc gaggtgagcc ccacgttctg cttcactctc ccatctccc     480 cccctcccc accccaatt ttgtatttat ttattttta attattttgt gcagcgatgg      540 gggcggggg gggggggggg cgcgcgccag gcggggcggg gcgggggcgag gggcggggcg    600 gggcgaggcg gagaggtgcg gcggcagcca atcagagcgg cgcgctccga aagtttcctt   660
ttatggcgag gcggcggcgg cggcggccct ataaaaagcg aagcgcgcgg cgggcgggag   720
tcgctgcgcg ctgccttcgc cccgtgcccc gctccgccgc cgcctcgcgc cgcccgcccc   780
ggctctgact gaccgcgtta ctcccacagg tgagcgggcg ggacgcccct tctcctccgg   840
gctgtaatta gcgcttggtt taatgacggc ttgtttcttt tctgtggctg cgtgaaagcc   900
ttgaggggct ccgggagggc cctttgtgcg ggggagcgg ctcggggctg tccgcggggg    960
gacggctgcc ttcgggggggg acgggcagg gcggggttcg gcttctggcg tgtgaccggc  1020
ggctctagag cctctgctaa ccatgttcat gccttcttct ttttcctaca gctcctgggc   1080
aacgtgctgg ttattgtgct gtctcatcat tttggcaaag aattggatcc actcgagtgg   1140
agctcgcgac tagtcgattc gaattcgtcg actggatcca gtaccgagga gatctgcgcc   1200
gcgatcgctg ctggaagctt actgcatatt tgatgtatta gagtgaaaac ctaatcatgc   1260
agttgttcat cctcattaat atggataagt catgtgttca tctttcattc taatttaatt   1320
caactgggcc ttttaatatt tcagcctcac cacttgctgg gctctgatcc ttcttttttct  1380 tctgcctcct cacgtctcca accagaaggt gatcttttag tccttcactt catggggagc   1440
cttcagagag agtaatgcag ccaccagaaa ggatgccgtt gaccgacaca gtgactgaca   1500
ggctgccctg gctcagttat cacagtgctg atgctgtcta ttctaaaggt acagtactgt   1560
gataactgaa ggatggcagc catcttacct tccatcagag gagcctcacc gtacccagga   1620
agaaagaagg tgaaagagga atgtgaaaca ggtggctggg acccagaaac cctcttaccc   1680
tgcacctctg tcatacttct cccggggcat agggagagtt attctgcttc tctttgcctt   1740
gttttgtaac atggggtagt tgttggtgca gccatgttgt gctgagtgaa catatattaa   1800
gatctttgga acctttagga gactgaaaat aggtaagtat gaattagtat ttctggaatg   1860
gtattcagag aacttcgacg cgtacgcggc cgctcgagca gaaactcatc tcagaagagg   1920
atctggcagc aaatgatatc aagcttatcg ataatcaacc tctggattac aaaatttgtg   1980
aaagattgac tggtattctt aactatgttg ctccttttac gctatgtgga tacgctgctt   2040
taatgccttt gtatcatgct attgcttccc gtatggcttt cattttctcc tccttgtata   2100
aatcctggtt gctgtctctt tatgaggagt tgtggcccgt tgtcaggcaa cgtggcgtgg   2160
tgtgcactgt gtttgctgac gcaacccccca ctggttgggg cattgccacc acctgtcagc   2220
tcctttccgg gactttcgct ttccccctcc ctattgccac ggcggaactc atcgccgcct   2280
gccttgcccg ctgctggaca ggggctcggc tgttgggcac tgacaattcc gtggtgttgt   2340
cggggaaatc atcgtccttt ccttggctgc tcgcctgtgt tgccacctgg attctgcgcg   2400
ggacgtcctt ctgctacgtc ccttcggccc tcaatccagc ggaccttcct tcccgcggcc   2460
tgctgccggc tctgcggcct cttccgcgtc ttcgccttcg ccctcagacg agtcggatct   2520
ccctttgggc cgcctccccg catcgatacc gtcgactcgc tgatcagcct cgactgtgcc   2580
ttctagttgc cagccatctg ttgtttgccc ctccccgtg ccttccttga ccctggaagg   2640
tgccactccc actgtccttt cctaataaaa tgaggaaatt gcatcgcatt gtctgagtag   2700
```

```
gtgtcattct attctggggg gtggggtggg gcaggacagc aaggggggagg attgggaaga    2760 caatagcagg catgctgggg atgcggtggg ctctatggct tctgaggcgg aaagaaccag    2820
ctggggctcg actagagcat ggctacgtag ataagtagca tggcgggtta atcattaact    2880
acaaggaacc cctagtgatg gagttggcca ctccctctct gcgcgctcgc tcgctcactg    2940
aggccgggcg accaaaggtc gcccgacgcc cgggctttgc ccggcggcc  tcagtgagcg    3000 agcgagcgcg cagagctttt tgcaaaagcc taggcctcca aaaagcctc  ctcactactt    3060 ctggaatagc tcagaggccg aggcggcctc ggcctctgca taaataaaaa aaattagtca    3120
gccatggggc ggagaatggg cggaactggg cggagttagg ggcgggatgg gcggagttag    3180
gggcgggact atggttgctg actaattgag atgcatgctt tgcatacttc tgcctgctgg    3240
ggagcctggg gactttccac acctggttgc tgactaattg agatgcatgc tttgcatact    3300
tctgcctgct ggggagcctg ggactttcc  acaccctaac tgacacacat tccacagctg    3360
cattaatgaa tcggccaacg cgcgggaga ggcggtttgc gtattgggcg ctcttccgct    3420
tcctcgctca ctgactcgct gcgctcggtc gttcggctgc ggcgagcggt atcagctcac    3480
tcaaaggcgg taatacggtt atccacagaa tcagggggata acgcaggaaa gaacatgtga    3540
gcaaaaggcc agcaaaaggc caggaaccgt aaaaaggccg cgttgctggc gttttttccat   3600 aggctccgcc cccctgacga gcatcacaaa aatcgacgct caagtcagag gtggcgaaac    3660
ccgacaggac tataaagata ccaggcgttt ccccctggaa gctccctcgt gcgctctcct    3720
gttccgaccc tgccgcttac cggatacctg tccgcctttc tcccttcggg aagcgtggcg    3780
ctttctcata gctcacgctg taggtatctc agttcggtgt aggtcgttcg ctccaagctg    3840
ggctgtgtgc acgaaccccc cgttcagccc gaccgctgcg ccttatccgg taactatcgt    3900
cttgagtcca acccggtaag acacgactta tcgccactgg cagcagccac tggtaacagg    3960
attagcagag cgaggtatgt aggcggtgct acagagttct tgaagtggtg gcctaactac    4020
ggctacacta agaaacagt  atttggtatc tgcgctctgc tgaagccagt taccttcgga    4080
aaaagagttg gtagctcttg atccggcaaa caaaccaccg ctggtagcgg tggttttttt    4140
gtttgcaagc agcagattac gcgcagaaaa aaaggatctc aagaagatcc tttgatcttt    4200
tctacggggt ctgacgctca gtggaacgaa aactcacgtt aagggatttt ggtcatgaga    4260
ttatcaaaaa ggatcttcac ctagatcctt taaattaaa  aatgaagttt taaatcaatc    4320
taaagtatat atgagtaaac ttggtctgac agttaccaat gcttaatcag tgaggcacct    4380
atctcagcga tctgtctatt tcgttcatcc atagttgcct gactccccgt cgtgtagata    4440
actacgatac gggagggctt accatctggc cccagtgctg caatgatacc gcgagaccca    4500
cgctcaccgg ctccagattt atcagcaata aaccagccag ccggaagggc cgagcgcaga    4560
agtggtcctg caactttatc cgcctccatc cagtctatta attgttgccg ggaagctaga    4620
gtaagtagtt cgccagttaa tagtttgcgc aacgttgttg ccattgctac aggcatcgtg    4680
gtgtcacgct cgtcgtttgg tatggcttca ttcagctccg gttcccaacg atcaaggcga    4740
gttacatgat cccccatgtt gtgcaaaaaa gcggttagct ccttcggtcc tccgatcgtt    4800
gtcagaagta agttggccgc agtgttatca ctcatggtta tggcagcact gcataattct    4860
cttactgtca tgccatccgt aagatgcttt tctgtgactg gtgagtactc aaccaagtca    4920
ttctgagaat agtgtatgcg gcgaccgagt tgctcttgcc cggcgtcaat acgggataat    4980
accgcgccac atagcagaac tttaaaagtg ctcatcattg gaaaacgttc ttcggggcga    5040
aaactctcaa ggatcttacc gctgttgaga tccagttcga tgtaacccac tcgtgcaccc    5100
```

```
aactgatctt cagcatcttt tactttcacc agcgtttctg ggtgagcaaa acaggaagg      5160 caaaatgccg caaaaaggg aataagggcg cacggaaat gttgaatact catactcttc       5220 cttttcaat attattgaag catttatcag ggttattgtc tcatgagcgg atacatattt      5280
gaatgtattt agaaaaataa acaaataggg gttccgcgca catttccccg aaaagtgcca    5340
cctgacgtct aagaaaccat tattatcatg acattaacct ataaaaatag gcgtatcacg    5400
aggccctttc gtctcgcgcg tttcggtgat gacggtgaaa acctctgaca catgcagctc    5460
ccggagacgg tcacagcttg tctgtaagcg gatgccggga gcagacaagc ccgtcagggc    5520
gcgtcagcgg gtgttggcgg gtgtcggggc tggcttaact atgcggcatc agagcagatt   5580
gtactgagag tgcaccattc gacgctctcc cttatgcgac tcctgcatta ggaagcagcc    5640
cagtagtagg ttgaggccgt tgagcaccgc cgccgcaagg aatggtgcat gcaaggagat   5700
ggcgcccaac agtccccgg ccacggggcc tgccaccata cccacgccga aacaagcgct     5760
catgagcccg aagtggcgag cccgatcttc cccatcggtg atgtcggcga taggcgcc     5820 agcaaccgca cctgtggcgc cggtgatgcc ggccacgatg cgtccggcgt agaggatctg    5880
gctagcgatg accctgctga ttggttcgct gaccatttcc gggtgcggga cggcgttacc    5940
agaaactcag aaggttcgtc caaccaaacc gactctgacg gcagtttacg agagagatga    6000
tagggtctgc ttcagtaagc cagatgctac acaattaggc ttgtacatat tgtcgttaga    6060
acgcggctac aattaataca taaccttatg tatcatacac atacgattta ggtgacacta    6120
tagaatacac ggaattaatt c                                              6141

<210> SEQ ID NO 4
<211> LENGTH: 6124
<212> TYPE: DNA
<213> ORGANISM: Artificial Sequence
<220> FEATURE:
<223> OTHER INFORMATION: Synthetic construct: pAM/CBA-miR128-2-WPRE-
      BGHpA

<400> SEQUENCE: 4
tagctgcgcg ctcgctcgct cactgaggcc gcccgggcaa agcccgggcg tcgggcgacc      60
tttggtcgcc cggcctcagt gagcgagcga gcgcgcagag agggagtggc caactccatc    120
actaggggtt ccttgtagtt aatgattaac ccgccatgct acttatctac gtagccatgc    180
tctaggtacc attgacgtca ataatgacgt atgttcccat agtaacgcca atagggactt    240
tccattgacg tcaatgggtg gagtatttac ggtaaactgc ccacttggca gtacatcaag    300
tgtatcatat gccaagtacg ccccctattg acgtcaatga cggtaaatgg cccgcctggc    360
attatgccca gtacatgacc ttatgggact ttcctacttg gcagtacatc tacgtattag    420
tcatcgctat taccatggtc gaggtgagcc ccacgttctg cttcactctc cccatctccc    480 cccctcccc accccaatt ttgtatttat ttatttttta attatttgt gcagcgatgg       540 gggcggggg gggggggggg cgcgcgccag gcggggcggg gcgggggcgag gggcggggcg    600 ggcgaggcg gagaggtgcg gcggcagcca atcagagcgg cgcgctccga aagtttcctt    660
ttatggcgag gcggcggcgg cggcggccct ataaaaagcg aagcgcgcgg cgggcgggag   720
tcgctgcgcg ctgccttcgc cccgtgcccc gctccgccgc cgcctcgcgc cgcccgcccc    780
ggctctgact gaccgcgtta ctcccacagg tgagcgggcg gacggccct tctcctccgg    840 gctgtaatta gcgcttggtt taatgacggc ttgtttcttt tctgtggctg cgtgaaagcc   900
ttgaggggct ccgggagggc cctttgtgcg ggggagcgg ctcggggctg tccgcggggg   960
```

```
gacggctgcc ttcggggggg acggggcagg gcggggttcg gcttctggcg tgtgaccggc    1020
ggctctagag cctctgctaa ccatgttcat gccttcttct ttttcctaca gctcctgggc    1080
aacgtgctgg ttattgtgct gtctcatcat tttggcaaag aattggatcc actcgagtgg    1140
agctcgcgac tagtcgattc gaattcgtcg actggatcca gtaccgagga gatctgcgcc    1200
gcgatcgcgt ctccataaat tattttttga tccttcttct gttaaagcag aaagtcaacc    1260
atgtccgtac ctttctagtt cataccttct tttaattttt tttttctttt caatttgaag    1320
agagtgcttc ctctgttctt aaggctaggg aaccaaatta ggttgtttca atatcgtgct    1380
aaaagatact gcctttagaa gaaggctatt gacaatccag cgtgtctcgg tggaactctg    1440
actccatggt tcactttcat gatggccaca tgcctcctgc ccagagcccg gcagccactg    1500
tgcagtggga agggggccg atacactgta cgagagtgag tagcaggtct cacagtgaac    1560
cggtctcttt ccctactgtg tcacactcct aatggaatgc cgttatccaa agagcagcac    1620
gaacccgaca gggctgagtg gcttgtgcta gggagaggtt tgtgtcattc ctgctgacca    1680
aactgcagga aaaactgcta attgtcatgc tgaagactgc ctgacgggga gactctgcct    1740
tctgtaagta ggtcatgtaa agagcacgtg ctccttgctg ctactcatag atgcctgctc    1800
cgtgatctga tttctgcact gaatctatgt tatgcatatg gaatgtatac agatacatgt    1860
acgcgtacgc ggccgctcga gcagaaactc atctcagaag aggatctggc agcaaatgat    1920
atcaagctta tcgataatca acctctggat tacaaaattt gtgaaagatt gactggtatt    1980
cttaactatg ttgctccttt tacgctatgt ggatacgctg cttta atgcc tttgtatcat    2040 gctattgctt cccgtatggc tttcattttc tcctccttgt ataaatcctg gttgctgtct    2100
ctttatgagg agttgtggcc cgttgtcagg caacgtggcg tggtgtgcac tgtgtttgct    2160
gacgcaaccc ccactggttg gggcattgcc accacctgtc agctcctttc cgggactttc    2220
gctttccccc tccctattgc cacggcggaa ctcatcgccg cctgccttgc ccgctgctgg    2280
acaggggctc ggctgttggg cactgacaat tccgtggtgt tgtcggggaa atcatcgtcc    2340
tttccttggc tgctcgcctg tgttgccacc tggattctgc gcgggacgtc cttctgctac    2400
gtcccttcgg ccctcaatcc agcggacctt ccttcccgcg gcctgctgcc ggctctgcgg    2460
cctcttccgc gtcttcgcct tcgccctcag acgagtcgga tctcccttg gccgcctcc     2520 ccgcatcgat accgtcgact cgctgatcag cctcgactgt gccttctagt tgccagccat    2580
ctgttgtttg cccctccccc gtgccttcct gaccctgga aggtgccact cccactgtcc     2640
tttcctaata aaatgaggaa attgcatcgc attgtctgag taggtgtcat tctattctgg    2700
ggggtggggt ggggcaggac agcaagggg aggattggga agacaatagc aggcatgctg    2760
gggatgcggt gggctctatg gcttctgagg cggaaagaac cagctgggc tcgactagag    2820 catggctacg tagataagta gcatggcggg ttaatcatta actacaagga acccctagtg    2880
atggagttgg ccactccctc tctgcgcgct cgctcgctca ctgaggccgg gcgaccaaag    2940
gtcgcccgac gcccgggctt tgcccgggcg gcctcagtga gcgagcgagc gcgcagagct    3000
ttttgcaaaa gcctaggcct ccaaaaaagc ctcctcacta cttctggaat agctcagagg    3060
ccgaggcggc ctcggcctct gcataaataa aaaaaattag tcagccatgg ggcggagaat    3120
gggcggaact gggcggagtt aggggcggga tgggcggagt taggggcggg actatggttg    3180
ctgactaatt gagatgcatg ctttgcatac ttctgcctgc tggggagcct ggggactttc    3240
cacacctggt tgctgactaa ttgagatgca tgctttgcat acttctgcct gctggggagc    3300
```

-continued

```
ctggggactt tccacaccct aactgacaca cattccacag ctgcattaat gaatcggcca    3360
acgcgcgggg agaggcggtt tgcgtattgg gcgctcttcc gcttcctcgc tcactgactc    3420
gctgcgctcg gtcgttcggc tgcggcgagc ggtatcagct cactcaaagg cggtaatacg    3480
gttatccaca gaatcagggg ataacgcagg aaagaacatg tgagcaaaag gccagcaaaa    3540
ggccaggaac cgtaaaaagg ccgcgttgct ggcgtttttc cataggctcc gcccccctga    3600
cgagcatcac aaaaatcgac gctcaagtca gaggtggcga acccgacag gactataaag     3660
ataccaggcg tttccccctg gaagctccct cgtgcgctct cctgttccga ccctgccgct    3720
taccggatac ctgtccgcct ttctcccttc gggaagcgtg gcgctttctc atagctcacg    3780
ctgtaggtat ctcagttcgg tgtaggtcgt tcgctccaag ctgggctgtg tgcacgaacc    3840
ccccgttcag cccgaccgct gcgccttatc cggtaactat cgtcttgagt ccaacccggt    3900
aagacacgac ttatcgccac tggcagcagc cactggtaac aggattagca gagcgaggta    3960
tgtaggcggt gctacagagt tcttgaagtg gtggcctaac tacggctaca ctagaagaac    4020
agtatttggt atctgcgctc tgctgaagcc agttaccttc ggaaaaagag ttggtagctc    4080
ttgatccggc aaacaaacca ccgctggtag cggtggtttt tttgtttgca agcagcagat    4140
tacgcgcaga aaaaaggat ctcaagaaga tcctttgatc ttttctacgg ggtctgacgc      4200
tcagtggaac gaaaactcac gttaagggat tttggtcatg agattatcaa aaaggatctt    4260
cacctagatc cttttaaatt aaaaatgaag ttttaaatca atctaaagta tatatgagta    4320
aacttggtct gacagttacc aatgcttaat cagtgaggca cctatctcag cgatctgtct    4380
atttcgttca tccatagttg cctgactccc cgtcgtgtag ataactacga tacgggaggg    4440
cttaccatct ggccccagtg ctgcaatgat accgcgagac ccacgctcac cggctccaga    4500
tttatcagca ataaaccagc cagccggaag ggccgagcgc agaagtggtc ctgcaacttt    4560
atccgcctcc atccagtcta ttaattgttg ccgggaagct agagtaagta gttcgccagt    4620
taatagtttg cgcaacgttg ttgccattgc tacaggcatc gtggtgtcac gctcgtcgtt    4680
tggtatggct tcattcagct ccggttccca acgatcaagg cgagttacat gatcccccat    4740
gttgtgcaaa aaagcggtta gctccttcgg tcctccgatc gttgtcagaa gtaagttggc    4800
cgcagtgtta tcactcatgg ttatggcagc actgcataat tctcttactg tcatgccatc    4860
cgtaagatgc ttttctgtga ctggtgagta ctcaaccaag tcattctgag aatagtgtat    4920
gcggcgaccg agttgctctt gcccggcgtc aatacgggat aataccgcgc cacatagcag    4980
aactttaaaa gtgctcatca ttggaaaacg ttcttcgggg cgaaaactct caaggatctt    5040
accgctgttg agatccagtt cgatgtaacc cactcgtgca cccaactgat cttcagcatc    5100
ttttactttc accagcgttt ctgggtgagc aaaaacagga aggcaaaatg ccgcaaaaaa    5160
gggaataagg gcgacacgga aatgttgaat actcatactc ttccttttc aatattattg     5220
aagcatttat cagggttatt gtctcatgag cggatacata tttgaatgta tttagaaaaa    5280
taaacaaata ggggttccgc gcacatttcc ccgaaaagtg ccacctgacg tctaagaaac    5340
cattattatc atgacattaa cctataaaaa taggcgtatc acgaggccct ttcgtctcgc    5400
gcgtttcggt gatgacggtg aaaacctctg acacatgcag ctcccggaga cggtcacagc    5460
ttgtctgtaa gcggatgccg ggagcagaca agcccgtcag ggcgcgtcag cgggtgttgg    5520
cgggtgtcgg gctggctta actatgcggc atcagagcag attgtactga gagtgcacca    5580
ttcgacgctc tcccttatgc gactcctgca ttaggaagca gcccagtagt aggttgaggc    5640
cgttgagcac cgccgccgca aggaatggtg catgcaagga gatggcgccc aacagtcccc    5700
```

```
cggccacggg gcctgccacc atacccacgc cgaaacaagc gctcatgagc ccgaagtggc    5760
gagcccgatc ttccccatcg gtgatgtcgg cgatataggc gccagcaacc gcacctgtgg    5820
cgccggtgat gccggccacg atgcgtccgg cgtagaggat ctggctagcg atgaccctgc    5880
tgattggttc gctgaccatt tccgggtgcg gacggcgtt accagaaact cagaaggttc      5940
```

```
gtccaaccaa accgactctg acggcagttt acgagagaga tgatagggtc tgcttcagta    6000
agccagatgc tacacaatta ggcttgtaca tattgtcgtt agaacgcggc tacaattaat    6060
acataacctt atgtatcata cacatacgat ttaggtgaca ctatagaata cacggaatta    6120
attc                                                                  6124
```

<210> SEQ ID NO 5
<211> LENGTH: 738
<212> TYPE: PRT
<213> ORGANISM: Artificial Sequence
<220> FEATURE:
<223> OTHER INFORMATION: AAVRec3 Amino Acid Sequence

<400> SEQUENCE: 5

```
Met Ala Ala Asp Gly Tyr Leu Pro Asp Trp Leu Glu Gly Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Arg Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Ala Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Lys Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
```

```
              275                 280                 285
Arg Phe His Cys His Phe Ser Pro Arg Asp Trp Gln Arg Leu Ile Asn
290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
                340                 345                 350

Leu Pro Tyr Val Leu Gly Ser Ala His Gln Gly Cys Leu Pro Pro Phe
                355                 360                 365

Pro Ala Asp Val Phe Met Ile Pro Gln Tyr Gly Tyr Leu Thr Leu Asn
370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Thr Phe Glu Asp Val Pro Phe His Ser Ser Tyr Ala His Ser Gln Ser
                420                 425                 430

Leu Asp Arg Leu Met Asn Pro Leu Ile Asp Gln Tyr Leu Tyr Tyr Leu
                435                 440                 445

Ser Arg Thr Gln Ser Thr Gly Gly Thr Gln Gly Thr Gln Gln Leu Leu
450                 455                 460

Phe Ser Gln Ala Gly Pro Ala Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
                500                 505                 510

Leu Asn Gly Arg Asp Ser Leu Val Asn Pro Gly Val Ala Met Ala Thr
                515                 520                 525

His Lys Asp Asp Glu Glu Arg Phe Phe Pro Ser Ser Gly Val Leu Met
530                 535                 540

Phe Gly Lys Gln Gly Ala Gly Arg Asp Asn Val Asp Tyr Ser Ser Val
545                 550                 555                 560

Met Leu Thr Ser Glu Glu Ile Lys Thr Thr Asn Pro Val Ala Thr
                565                 570                 575

Glu Gln Tyr Gly Val Val Ala Asp Asn Leu Gln Gln Thr Asn Thr Gly
                580                 585                 590

Pro Ile Val Gly Asn Val Asn Ser Gln Gly Ala Leu Pro Gly Met Val
                595                 600                 605

Trp Gln Asn Arg Asp Val Tyr Leu Gln Gly Pro Ile Trp Ala Lys Ile
                610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Asn Gln Ser Lys Leu Asn Ser Phe
                660                 665                 670

Ile Thr Gln Tyr Ser Thr Gly Gln Val Ser Val Glu Ile Glu Trp Glu
                675                 680                 685

Leu Gln Lys Glu Asn Ser Lys Arg Trp Asn Pro Glu Ile Gln Tyr Thr
690                 695                 700
```

```
Ser Asn Tyr Tyr Lys Ser Thr Ser Val Asp Phe Ala Val Asn Thr Glu
705                 710                 715                 720

Gly Val Tyr Ser Glu Pro Arg Pro Ile Gly Thr Arg Tyr Leu Thr Arg
            725                 730                 735

Asn Leu
```

USE OF MIR101 OR MIR128 IN THE TREATMENT OF SEIZURE DISORDERS

CROSS-REFERENCE TO RELATED APPLICATIONS

This application is a continuation application of U.S. patent application Ser. No. 16/211,309, filed Dec. 6, 2018, which claims benefit of and priority to U.S. Provisional Application No. 62/595,255, filed Dec. 6, 2017, which are incorporated by reference in their entireties.

TECHNICAL FIELD

Treatment of seizure disorders using micro RNAs MIR101 or MIR128.

BACKGROUND

Seizure disorders typically involve abnormal nerve cell activity in the brain, causing seizures which may be manifested by periods of unusual behavior, sensations, convulsions, diminished consciousness and sometimes loss of consciousness. Seizures can be a symptom of many different disorders that can affect the brain. Epilepsy is a seizure disorder characterized by recurrent seizures. See, e.g., Blume et al., Epilepsia. 2001; 42:1212-1218. Epileptic seizures are usually marked by abnormal electrical discharges in the brain and typically manifested by sudden brief episodes of altered or diminished consciousness, involuntary movements, or convulsions.

Seizures can be categorized as focal seizures (also referred to as partial seizures) and generalized seizures. Focal seizures affect only one side of the brain, while generalized seizures affect both sides of the brain. Specific types of focal seizures include simple focal seizures, complex focal seizures, and secondarily generalized seizures. Simple focal seizures can be restricted or focused on a particular lobe (e.g., temporal lobe, frontal lobe, parietal lobe, or occipital lobe). Complex focal seizures generally affect a larger part of one hemisphere than simple focal seizures, but commonly originate in the temporal lobe or the frontal lobe. When a focal seizure spreads from one side (hemisphere) to both sides of the brain, the seizure is referred to as a secondarily generalized seizure. Specific types of generalized seizures include absences (also referred to as petit mal seizures), tonic seizures, atonic seizures, myoclonic seizures, tonic clonic seizures (also referred to as grand mal seizures), and clonic seizures.

Examples of seizure disorders include epilepsy, epilepsy with generalized tonic-clonic seizures, epilepsy with myoclonic absences, frontal lobe epilepsy, temporal lobe epilepsy, Landau-Kleffner Syndrome, Rasmussen's syndrome, Dravet syndrome, Doose syndrome, CDKL5 disorder, infantile spasms (West syndrome), juvenile myoclonic epilepsy (JME), vaccine-related encephalopathy, intractable childhood epilepsy (ICE), Lennox-Gastaut syndrome (LGS), Rett syndrome, Ohtahara syndrome, CDKL5 disorder, childhood absence epilepsy, essential tremor, acute repetitive seizures, benign rolandic epilepsy, status epilepticus, refractory status epilepticus, super-refractory status epilepticus (SRSE), PCDH19 pediatric epilepsy, focal cortical dysplasia, and increased seizure activity or breakthrough seizures (also called serial or cluster seizures). Seizure disorders can be associated with a sodium channel protein type 1 subunit alpha (Scn1a)-related disorder.

Brain tumors of all types can be associated with seizure disorders. Certain tumors are associated with a greater frequency of seizures. For example, gangliogliomas are slow growing benign tumors which may occur in the spinal cord and/or temporal lobes. Gangliogliomas are composed of both neoplastic glial and ganglion cells which are disorganized, variably cellular, and non-infiltrative. Gangliogliomas are commonly associated with seizures. Gliomas are brain tumors that develop from glial cells in the brain. Gliomas are classified into four grades (I, II, III and IV), and the treatment and prognosis depend upon the tumor grade. Low grade gliomas originate from two different types of brain cells: astrocytes and oligodendrocytes. Low grade gliomas are classified as a grade 2 tumor making them the slowest growing type of glioma. Between 60 and 85 percent of people with low-grade glioma may experience a seizure. High grade gliomas (grade 3 or 4) are fast growing gliomas that typically present a poor prognosis. Grade 3 gliomas include anaplastic astrocytoma, anaplastic oligodendroglioma, anaplastic oligoastrocytoma, and anaplastic ependymoma. Glioblastomas are grade 4 gliomas. Seizures occur in more than half of patients with grade III gliomas and about one-quarter of patients with grade IV gliomas. Meningiomas are tumors that arise from the meninges—the membranes surrounding the brain and spinal cord. Although not technically located in the brain, meningiomas may compress or squeeze the adjacent brain, nerves and vessels. Meningioma is the most common type of tumor that forms in the head. Most meningiomas are slow growing. Seizures are associated with meningiomas.

Focal cortical dysplasia is a malformation of cortical development, which is a common cause of medically refractory epilepsy in the pediatric population and a common etiology of medically intractable seizures in adults. Focal cortical dysplasia (FCD) has been classified into three types and further sub-types. Type I is typically associated with temporal lobes—malformation presenting with abnormal cortical lamination as a result of abnormal radial migration and maturation of neurons (FCD Type Ia) or disruption of typical 6-layered tangential composition of the cortex with immature neurons (FCD Type Ib) or both architectural abnormalities, radial and tangential cortical lamination (FCD Type Ic). Type II is commonly found in frontal lobes—malformation resulting from disrupted cortical lamination and specific cytological abnormalities, Type IIa—dysmorphic neurons (without balloon cells) and Type IIb—dysmorphic neurons and balloon cells. Type III—malformation connected with different cortical dislamination and cytological abnormalities with main lesion within the same area/lobe. Type IIIa—in the temporal lobe, cortical dislayering with hippocampal atrophy, IIIb—adjacent to glial or glioneuronal tumors (DNET, ganglioglioma), IIIc—adjacent to vascular malformations (as hemangiomas, arteriovenous malformations, telangiectasias, etc), IIId—acquired at early age (trauma, ischemia or perinatal hemorrhage, infectious or inflammatory diseases). See, Kabat and Krol, Pol J Radiol, 2012, 77(2) 35-43. FCD may involve any part of the brain, may vary in size and location and may be multifocal. Seizures are the main symptom of FCD, sometimes associated with mental retardation, particularly with early seizure onset. Symptoms can appear at any age, mostly in childhood, but also can occur in adults. Seizures associated with FCD can be drug-resistant.

Hemartomas are a mostly benign, focal malformation that resembles a neoplasm in the tissue of its origin. They are composed of tissue elements normally found at that site, but grow in a disorganized manner. Hemartomas can originate in the brain. Tuberous Sclerosis Complex (TSC) is a genetic seizure disorder characterized by hamartomatous growth in various organs. Patients who have this disorder can exhibit a high rate of epilepsy and cognitive problems resulting from multiple lesions in the brain. TSC lesions (corticol tubers) typically contain dysmorphic neurons, brightly eosinophilic giant cells and white matter alterations. Seizures associated with TSC can be intractable. Tuber cinereum hamartoma (also known as hypothalamic hamartoma) is a benign tumor in which a disorganized collection of neurons and glia accumulate at the tuber cinereum of the hypothalamus. Symptoms include gelastic seizures, a disorder characterized by spells of involuntary laughter with interval irritability and depressed mood.

Medications used to treat seizure disorders can be referred to as anti-epileptic drugs ("AED"). The treatment of recurrent seizures predominantly centers on the utilization of at least one AED, with possible adjunctive use of a second or even third agent in the case of monotherapeutic failure. See, Tolman and Faulkner, Ther Clin Risk Manag. 2011; 7: 367-375. However, approximately 30%-40% of epileptic patients have inadequate seizure control with just one AED, and require the use of adjunctive agents. Id. A subset of this group will have regular and persistent seizure activity despite reasonable doses of multiple AEDs. These seizures are considered refractory to treatment. Id. Accordingly, there remains a need for improved and/or additional therapies for treating seizure disorders.

MicroRNAs (miRNAs) are short (20-24 nt) non-coding RNAs that are involved in post-transcriptional regulation of gene expression in multicellular organisms by affecting both the stability and translation of mRNAs. miRNAs are transcribed by RNA polymerase II as part of capped and polyadenylated primary transcripts (pri-miRNAs) that can be either protein-coding or non-coding. pri-miRNAs are processed into ~70 nt hairpin structures known as precursors (pre-miRNAs). Pre-miRNAs are transported from the nucleus to the cytoplasm, where they are processed into ~22 bp double stranded RNAs by the RISC loading complex. The mature miRNA is incorporated into a RNA-induced silencing complex (RISC), which recognizes target mRNAs through imperfect base pairing with the miRNA and most commonly results in translational inhibition or destabilization of the target mRNA.

MicroRNA 101 (also referred to as MIR101, miR101, miR-101 or miRNA-101) has been identified in connection with inhibition of expression and function of EZH2 in cancer cell lines. See, Varambally et al., Science 2008, 322: 1695-1699. There are two miR-101 isoforms: miR-101-1 and miR-101-2 in humans and miR-101a and miR-101b in mice. See, Huang et al., Journal of Biological Chemistry, 2017, 292, 16420-16439. All of the miR-101 isoforms have the same mature sequence, with the exception of miR-101b, which has one base difference. Id. The mature sequence of human miR101 is UACAGUACUGUGAUAACUGAA [SEQ ID NO:1]. Lippi et al., Neuron 2016, 92(6), 1337-1351, indicates that miR-101 regulates multiple post-natal developmental programs in parallel to constrain excitatory activity in adult rodents. Lippi et al., identified miR-101a and miR-101b as being highly expressed on post-natal day 12 from RNA sequencing of the mouse hippocampus. Lippi et al. posit that transient miR-101 inhibition in early life produces hyperexcitable networks in the adult. Although miR-101 inhibition led to the appearance of spontaneous high-frequency burst discharges that resembled spontaneous seizure-like events, Lippi et al. conclude that the network does not exhibit full epileptic phenotype.

MicroRNA 128 (also referred to as MIR128, miR-128 or miRNA-128) is encoded by two separate genes, miR-128-1 and miR-128-2, on mouse chromosomes 1 and 9 or human chromosomes 2 and 3, respectively. Tan, et al. Science 2013, 342(6163):1254-1258. MicroRNA 128-2 (also referred to as MIR128-2 or miR128-2) is one of the most abundant and highest enriched miRNA in the adult mouse and human brain. Id. The mature sequence of miR128 is GGGGGCCGAUACACUGUACGAGA [SEQ ID NO:2]. In mice, germline miR-128-2 deficiency results in an 80% reduction of miR-128 expression in the forebrain, whereas ablation of the miR-128-1 gene eliminates only 20% of miR-128. Id. Tan et al. determined that in mice, a reduction of miR-128 expression in postnatal neurons causes increased motor activity and fatal epilepsy. Overexpression of miR-128 attenuates neuronal responsiveness, suppresses motor activity and alleviates motor abnormalities associated with Parkinson's—like disease and seizures in mice. Id.

The blood brain barrier (BBB) prevents many compounds in the blood stream from entering the tissues and fluids of the brain. The BBB is formed by brain-specific endothelial cells and supported by the cells of the neurovascular unit to limit the passage of polar molecules or large molecules such as proteins and peptides into or out of the brain interstitium. However, the BBB also prevents many therapeutic compounds from entering the brain which can interfere with effective treatment of brain conditions and diseases.

One method of assisting transport of therapeutic drugs through the BBB involves delivering ultrasound energy to the BBB which "opens up" the BBB and interferes with the ability of the BBB to prevent transport of therapeutic agents into the brain. See, e.g., U.S. Pat. No. 5,752,515, which is directed to image guided ultrasound delivery of compounds through the BBB. In one aspect, the change induced in the central nervous system (CNS) tissues and/or fluids by ultrasound is by heating or cavitation. Such heating or cavitation may present a drawback since it may cause damage to tissues and potentially degrade the compounds being delivered for therapeutic benefit. Ultrasound also causes degradation of organic compounds. See, e.g., Bremner et al., Current Organic Chemistry, 15(2): 168-177 (2011) ("Bremner et al."). According to Bremner et al., when aqueous solutions are irradiated with ultrasound, the H—O bond in water is homolytically cleaved to form hydroxyl radicals and hydrogen atoms. This process is the result of cavitation, whereby very high temperatures and pressures are generated within an imploding bubble. Id. Accordingly, use of ultrasound in an attempt to open the BBB to cause or increase delivery of therapeutic compounds to the brain could degrade them and interfere with or prevent therapeutic treatment.

SUMMARY

A method of treating a seizure disorder in a patient in need thereof is provided which includes delivering to the patient an effective amount of a composition that increases the level of microRNA-101 molecules in brain cells of the patient. A method of treating a seizure disorder in a patient in need thereof is provided which includes delivering to the patient an effective amount of a composition that increases the level of microRNA-128 molecules in brain cells of the patient. A method of treating a seizure disorder in a patient in need thereof is provided which includes administering a vector encoding microRNA-101, pri-miR101 or pre-miR101 to the patient. A method of treating a seizure disorder in a patient in need thereof is provided which includes administering a vector encoding microRNA-128, pri-miR128 or pre-miR128 to the patient. In embodiments, increased levels of microRNA-101 or microRNA-128 cause improvement in one or more symptoms of the seizure disorder.

In embodiments, a vector encoding microRNA-101, pri-miR101 or pre-miR101, causes increased levels of microRNA-101 in a patient with a seizure disorder and is associated with reduced symptoms of the seizure disorder. In embodiments, a vector encoding microRNA-128, pri-miR128 or pre-miR128 causes increased levels of microRNA-128 in a patient with a seizure disorder and is associated with reduced symptoms of the seizure disorder.

In embodiments, a vector including nucleic acid encoding microRNA-101, pri-miR101 or pre-miR101, includes a promoter operatively linked to the nucleic acid encoding microRNA-101, pri-miR101 or pre-miR101. In embodiments, the vector includes a woodchuck post-transcriptional regulatory element (WPRE). In embodiments, the vector includes a bovine growth hormone polyadenylation sequence (BGHpA). In embodiments, the vector includes a fluorescence reporter cassette. In embodiments, the vector is an adeno-associated virus. In embodiments, the vector is a lentivirus. In embodiments, a vector including nucleic acid encoding microRNA-128, pri-miR128 or pre-miR128, includes a promoter operatively linked to the nucleic acid encoding microRNA-128, pri-miR128 or pre-miR128. In embodiments, the nucleic acid encoding microRNA-128 is microRNA-128-2. In embodiments, the vector includes a woodchuck post-transcriptional regulatory element (WPRE). In embodiments, the vector includes a bovine growth hormone polyadenylation sequence (BGHpA). In embodiments, the vector includes a fluorescence reporter cassette. In embodiments, the vector is an adeno-associated virus. In embodiments, the vector is a lentivirus. In embodiments, the vector is pAM/CBA-miR101-1-WPRE-BGHpA. In embodiments, the vector is pAM/CBA-miR128-2-WPRE-BGHpA.

In embodiments, the vector is delivered to a target location in the patient's brain. In embodiments, the target location is the frontal lobe, the temporal lobe, the occipital lobe or the parietal lobe. In embodiments, the route of administration of the vector is oral, buccal, sublingual, rectal, topical, intranasal, vaginal or parenteral. In embodiments, the vector is administered directly to the target location.

In embodiments, the seizure disorder is characterized by focal seizures. In embodiments, the seizure disorder is focal cortical dysplasia. In embodiments, the seizure disorder is epilepsy, epilepsy with generalized tonic-clonic seizures, epilepsy with myoclonic absences, frontal lobe epilepsy, temporal lobe epilepsy, occipital lobe epilepsy, parietal lobe epilepsy, Landau-Kleffner Syndrome, Rasmussen's syndrome, Dravet syndrome, Doose syndrome, CDKL5 disorder, infantile spasms (West syndrome), juvenile myoclonic epilepsy (JME), vaccine-related encephalopathy, intractable childhood epilepsy (ICE), Lennox-Gastaut syndrome (LGS), Rett syndrome, Ohtahara syndrome, CDKL5 disorder, childhood absence epilepsy, essential tremor, acute repetitive seizures, benign rolandic epilepsy, status epilepticus, refractory status epilepticus, super-refractory status epilepticus (SRSE), PCDH19 pediatric epilepsy, brain tumor induced seizures, hamartoma induced seizures, drug withdrawal induced seizures, alcohol withdrawal induced seizures, increased seizure activity or breakthrough seizures.

In embodiments, ultrasound is applied to a target location in the patient's brain to enhance permeability of the patient's blood brain barrier at a target location, wherein microRNA-101 or microRNA-128 is delivered to the target location.

BRIEF DESCRIPTION OF THE DRAWINGS

FIGS. 2A, 2B, 2C and 2D depict the nucleotide sequence of pAM/CBA-miR101-1-WPRE-BGHpA [SEQ ID NO:3].

FIGS. 6A, 6B, 6C and 6D depict the nucleotide sequence of pAM/CBA-miR128-2-WPRE-BGHpA [SEQ ID NO:4].

FIG. 8 depicts the amino acid sequence of AAVRec3 [SEQ ID NO:5].

DETAILED DESCRIPTION

Figure 1:
FIG. 1 is a plasmid map of pAM/CBA-miR101-1-WPRE-BGHpA.

Described herein are methods and compositions for treating a seizure disorder which include administering microRNA-101, pri-miR101 or pre-miR101, to a patient having a seizure disorder. Also described herein are methods and compositions for treating a seizure disorder which include administering microRNA-128, pri-miR128 or pre-miR128, to a patient having a seizure disorder. In embodiments, vectors encoding microRNA-101, pri-miR101 or pre-miR101 are provided. In embodiments, vectors encoding microRNA-101, pri-miR101 or pre-miR101 are administered to a patient having a seizure disorder wherein the patient exhibits improvement in one or more symptoms of the seizure disorder. In embodiments, vectors encoding microRNA-128, pri-miR128 or pre-miR128 are provided. In embodiments, vectors encoding microRNA-128, pri-miR128 or pre-miR128 are administered to a patient having a seizure disorder wherein the patient exhibits improvement in one or more symptoms of the seizure disorder. In embodiments, ultrasound is applied to a target location in the patient's brain to enhance permeability of the patient's blood brain barrier at a target location, wherein microRNA-101 or microRNA-128 is delivered to the target location.

MicroRNA-101, pri-miR101, pre-miR101, microRNA-128, pri-miR128, and/or pre-miR128, are collectively referred to herein as microRNA or microRNAs. Administration to a patient of microRNA-101, pri-miR101, pre-miR101, microRNA-128, pri-miR128, and/or pre-miR128, is collectively referred to herein as microRNA treatment. MicroRNA treatment increases the level of respective active microRNA molecules in a cell. The increase can come about by directly providing the microRNA to a cell, or may come about by indirectly providing microRNA to cell, such as through a vector. The microRNA may include a RNA or DNA molecule that also includes additional sequences. Increases in the level of respective active microRNA molecules in brain cells of a patient are associated with an improvement in one or more symptoms of a seizure disorder.

One or more pri-miRNA(s) can be used in the compositions and methods described herein. Any suitable form of a pri-mRNA can be used. The pri-mRNA(s) can be processed intracellularly and act to gain function for the miRNA, e.g., converted into pre-mRNA(s) and then the mature form. Alternatively, the miRNA may initially be a miRNA precursor. In embodiments, the compositions and methods include pre-miRNA, which is subject to cleavage by an RNAse III type double stranded endonuclease called Dicer, resulting in an imperfect miRNA:miRNA* duplex that is about 20-25 nucleotides in size. This duplex contains the mature miRNA strand and its opposite complementary miRNA* strand. One or more pre-miRNA(s) can be used in the compositions and methods described herein. The pre-miRNA may act to gain function for the miRNA. Any suitable form of a pre-miRNA can be used. It is also contemplated that the miRNA of the compositions and methods described herein may be mature miRNA.

The microRNAs can be delivered to cells in non-expression vector or expression vector modalities. Expression vector and vector are used interchangeably herein. In embodiments, microRNA may be isolated or purified prior to use in a subsequent step. MicroRNAs may be isolated or purified prior to introduction into a cell. "Introduction" into a cell includes known methods of transfection, transduction, infection and other methods for introducing an expression vector or a heterologous nucleic acid into a cell. A template nucleic acid or amplification primer may be isolated or purified prior to it being transcribed or amplified. Isolation or purification can be performed by a number of methods known to those of skill in the art with respect to nucleic acids. The delivery of the microRNA may occur through several forms, such as through encapsulation of a chemically modified or through an unmodified RNA moiety within a viral or non-viral delivery vessel. Non-expression vector delivery modalities include nanoparticles, microparticles, liposomes, polymers, microspheres, etc., which may be targeted to brain cells. The microRNA can also be delivered as a plasmid or minivector based expression system where it can then be expressed and processed by the RNAi machinery in cells to form a mature microRNA.

Nucleic acid constructs for miRNA expression may be produced recombinantly. Such expression vectors are provided herein. Expression vectors are a carrier nucleic acid into which a nucleic acid sequence can be inserted for introduction into a cell where it can be replicated. Expression vectors include plasmids, cosmids, recombinant viruses, such as adeno-associated virus (AAV), adenoviruses, retroviruses, poxviruses, and other known viruses in the art (bacteriophage, animal viruses, and plant viruses), and artificial chromosomes (e.g., YACs). A person of ordinary skill in the art is well equipped to construct expression vectors through standard recombinant techniques. In embodiments, an expression vector having an microRNA is delivered to cells of a patient. The nucleic acid molecules are delivered to the cells of a patient in a form in which they can be taken up and are advantageously expressed so that therapeutically effective levels can be achieved.

Any suitable expression vector known to those skilled in the art may be utilized to deliver microRNA(s) herein to a target location in the brain. Upon such delivery, neurons in the target locations are transfected with microRNA(s), thereby increasing levels of those microRNA(s) in the brain of the patient. Transducing viral (e.g., retroviral, adenoviral, lentiviral and adeno-associated viral) vectors can be used for somatic cell gene therapy, especially because of their high efficiency of infection and stable integration and expression.

In embodiments, the expression vector may be a stable integrating vector or a stable nonintegrating vector. Examples of suitable vectors are lentiviruses and adeno-associated viruses (AAV). Lentiviruses are a subclass of retroviruses. Lentiviruses can integrate into the genome of non-dividing cells such as neurons. Lentiviruses are characterized by high-efficiency infection, long-term stable expression of transgenes and low immunogenicity. In embodiments, lentiviral vectors may be utilized to deliver microRNA(s) to the brain.

AAV is a defective parvovirus known to infect many cell types and is nonpathogenic to humans. AAV can infect both dividing and non-dividing, cells. In embodiments, AAV vectors may be utilized herein to deliver microRNA(s) to the brain. Any of the known adeno-associated viruses (AAV) may be utilized herein, e.g., AAV1, AAV2, AAV4, AAV5, AAV8, AAV9 and AAVRec3 may be utilized in connection with neurons. Additional suitable AAV serotypes have been developed through pseudotyping, i.e., mixing the capsid and genome from different viral serotypes. Accordingly, e.g., AAV2/7 indicates a virus containing the genome of serotype 2 packaged in the capsid from serotype 7. Other examples are AAV2/5, AAV2/8, AAV2/9, etc. Hybrid AAV capsid serotypes rec1, rec2, rec3 and rec4 were generated by shuffling the fragments of capsid sequences that matched in all three non-human primate AAV serotypes cy5, rh20 and rh39, with AAV8. See, Charbel et al., PLoS One. 2013 Apr. 9; 8 (4):e60361. The terms rec3AAV and AAVRec3 may be used interchangeably herein. The amino acid sequence of AAVRec3 is depicted in FIG. 8. Self-complementary adeno-associated virus (scAAV) may also be utilized as vectors. Whereas AAV packages a single strand of DNA and requires the process of second-strand synthesis, scAAV packages both strands which anneal together to form double stranded DNA. By skipping second strand synthesis scAAV allows for rapid expression in the cell.

Suitable vectors may be constructed by those having ordinary skill in the art using known techniques. Suitable vectors can be chosen or constructed, containing, in addition to microRNA(s), appropriate regulatory sequences, including promoter sequences, terminator fragments, polyadenylation sequences, marker genes and other sequences as appropriate. Those skilled in the art are familiar with appropriate regulatory sequences, including promoter sequences, terminator fragments, polyadenylation sequences, marker genes and other suitable sequences.

Expression vectors herein include appropriate sequences operably linked to the coding sequence or ORF to promote its expression in a targeted host cell. "Operably linked" sequences include both expression control sequences such as promoters that are contiguous with the coding sequences and expression control sequences that act in trans or distally to control the expression of the desired product.

Typically, the vector includes a promoter to facilitate expression of the microRNA(s) within a target cell. The promoter may be selected from a number of constitutive or inducible promoters that can drive expression of the selected transgene in the brain. Examples of constitutive promoters include CMV immediate early enhancer/chicken beta-actin (CBA) promoter-exon 1-intron 1 element, RSV LTR promoter/enhancer, the SV40 promoter, the CMV promoter, dihydrofolate reductase (DHFR) promoter, and the phosphoglycerol kinase (PGK) promoter.

Specificity can be achieved by regional and cell-type specific expression of the receptor exclusively, e.g., using a tissue or region specific promoter. Virus gene promoter elements may help dictate the type of cells that express microRNA(s). Some promoters are nonspecific (e.g., CAG, a synthetic promoter), while others are neuronal-specific. The CAG promoter is a strong synthetic promoter that can be used to drive high levels of expression. The CAG promoter consists of 1) a cytomegalovirus (CMV) early enhancer element, 2) the promoter, the first exon and the first intron of the chicken beta-actin gene, and 3) the splice acceptor of the rabbit beta-globin gene. In embodiments the promoter is the CAG promoter. Neuronal specific promoters include (e.g., synapsin; hSyn), or preferential to specific neuron types, e.g., dynorphin, encephalin, GFAP (Glial fibrillary acidic protein) which is preferential to astrocytes, or CaMKIIa, which is preferential to cortical glutamatergic cells but can also target subcortical GABAergic cells. In embodiments, the promoter is the CamkIIa (alpha CaM kinase II gene) promoter, which may drive expression in the forebrain. Other neuronal cell type-specific promoters include the NSE promoter, tyrosine hydroxylase promoter, myelin basic protein promoter, glial fibrillary acidic protein promoter, and neurofilaments gene (heavy, medium, light) promoters.

Expression control sequences may also include appropriate transcription initiation, termination, and enhancer sequences; efficient RNA processing signals such as splicing and polyadenylation signals; sequences that stabilize cytoplasmic mRNA; sequences that enhance translation efficiency (e.g., Kozak consensus sequence); sequences that enhance nucleic acid or protein stability; and when desired, sequences that enhance product processing and/or secretion. Many varied expression control sequences, including native and non-native, constitutive, inducible and/or tissue-specific, are known in the art and may be utilized herein depending upon the type of expression desired.

In addition to promoters, expression control sequences for eukaryotic cells typically include an enhancer, such as one derived from an immunoglobulin gene, SV40, CMV, etc., and a polyadenylation sequence which may include splice donor and acceptor sites. The polyadenylation sequence generally is inserted 3' to the coding sequence and 5' to the 3' ITR sequence. Illustrative examples of polyA signals that can be used in a vector herein include polyA sequence (e.g., AATAAA, ATTAAA, or AGTAAA), a bovine growth hormone polyA sequence (BGHpA), a rabbit beta-globin polyA sequence (rBgpA), or another suitable heterologous or endogenous polyA sequence known in the art.

Regulatory sequences useful herein may also contain an intron, such as one located between the promoter/enhancer sequence and the coding sequence. One useful intron sequence is derived from SV40, and is referred to as the SV40 T intron sequence. Another includes the woodchuck hepatitis virus post-transcriptional element (WPRE). WPRE is a DNA sequence that, when transcribed, creates a tertiary structure that enhances expression.

Vectors herein may contain reporter genes, e.g., those which encode fluorophores. A fluorophore is a fluorescent compound that can re-emit light upon excitation, usually at specific frequencies. They can be used as a tag or marker which can be attached to, e.g., a protein to allow the protein to be located. Many suitable fluorophores are known in the art. They may be categorized by the color they emit, e.g., blue, cyan, green, yellow, orange, red and others. For example, mCherry, mRasberry, mTomato and mRuby are red fluorophore proteins; citrine, venus, and EYFP are yellow fluorophore proteins. Green fluorescent protein (GFP) is a commonly used fluorophore.

In embodiments, the expression vector is pAM/CBA-miR101-1-WPRE-BGHpA. A plasmid map of pAM/CBA-miR101-1-WPRE-BGHpA is depicted in FIG. 1. The nucleic acid sequence [SEQ ID NO:3] is shown in FIGS. 2A-2D. TABLE I annotates pAM/CBA-miR101-1-WPRE-BGHpA.

TABLE I

| Name | Type | Minimum | Maximum | Length | Direction |
|---|---|---|---|---|---|
| AmpR | CDS | 4353 | 5213 | 861 | reverse |
| pUC19 Ori | rep_origin | 3440 | 4227 | 788 | reverse |
| SV40 Ori | rep_origin | 3019 | 3354 | 336 | reverse |
| ITR | LTR | 2836 | 3018 | 183 | forward |
| BGHpA | polyA_signal | 2558 | 2826 | 269 | forward |
| WPRE | misc_feature | 1947 | 2539 | 593 | forward |
| miR101-1 | misc_feature | 1209 | 1877 | 669 | forward |
| CAG-promoter | promoter uukaryotic | 190 | 1125 | 936 | forward |
| ITR | LTR | 1 | 183 | 183 | forward |

Figure 3:
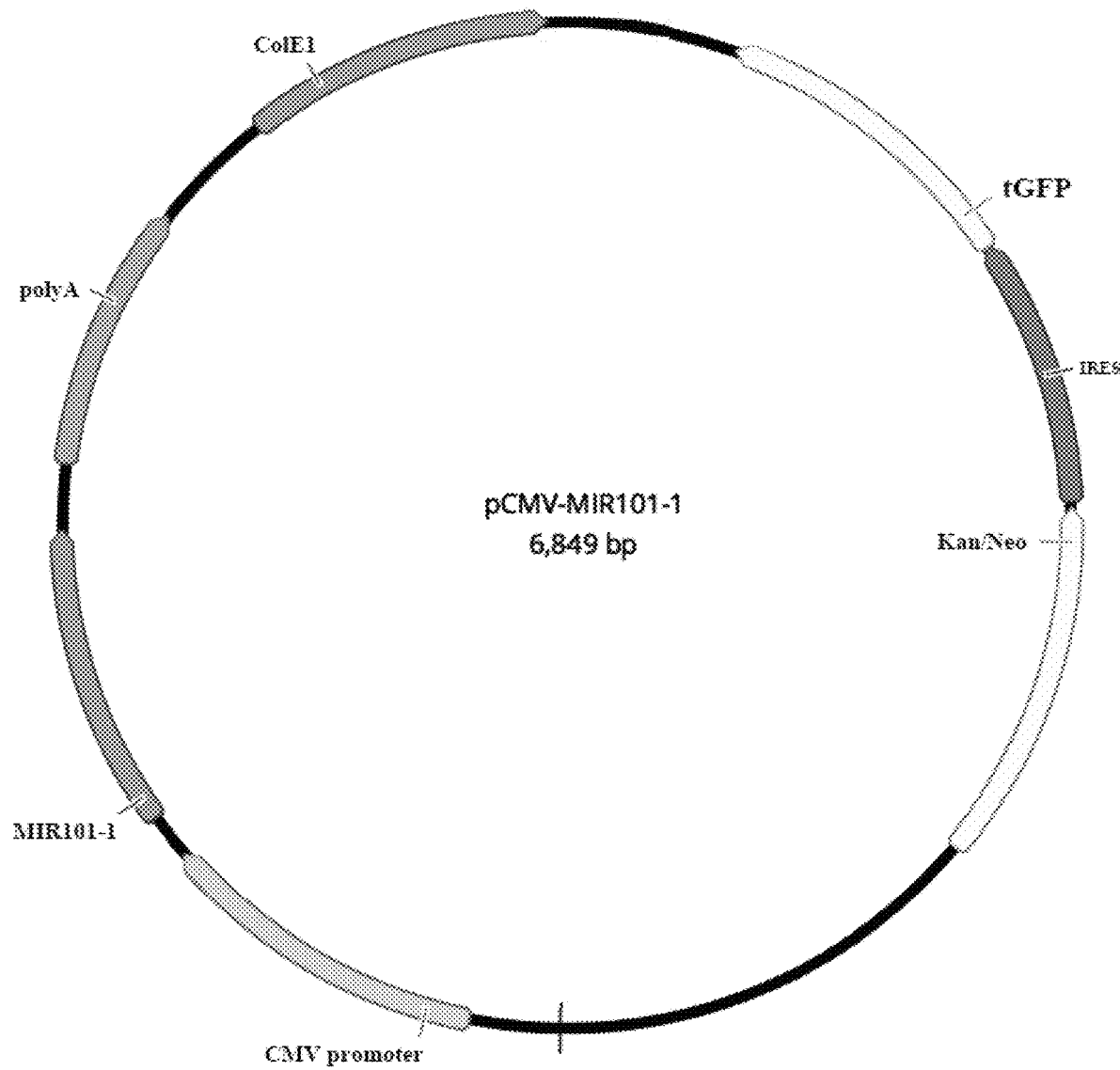
FIG. 3 is a plasmid map of pCMV-MIR101-1.
Figure 4:
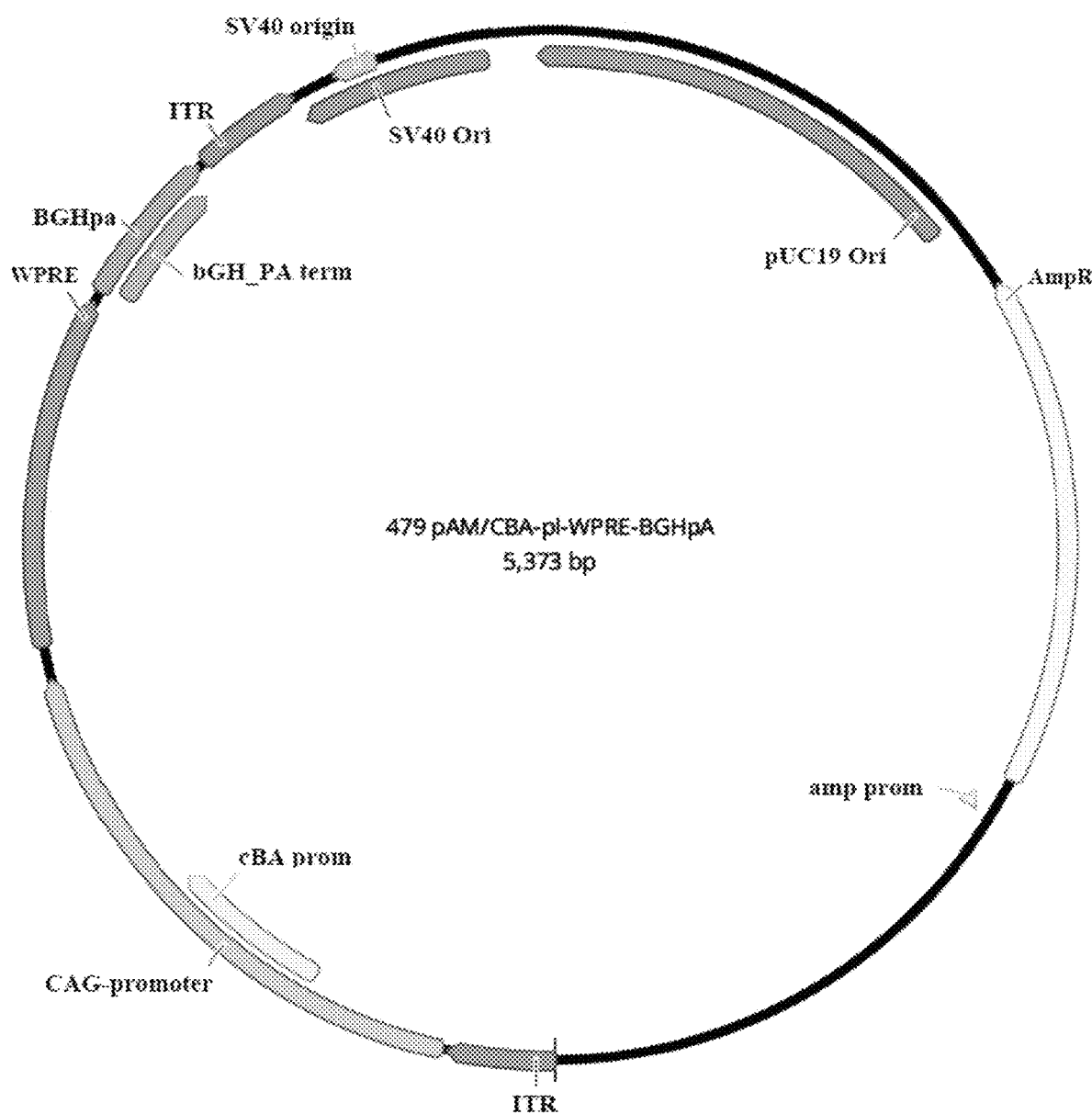
FIG. 4 is a plasmid map of pAM_CBA-pl-WPRE-BGHpA.

To construct pAM/CBA-miR101-1-WPRE-BGHpA, EcoRI-EcoRV fragments from the pCMV-MIR101-1 plasmid (772 bp) (SC400013), commercially available from OriGene Technologies, Inc., 9620 Medical Center Dr., Suite 200, Rockville, Md. 20850, is inserted into pAM_CBA-pl-WPRE-BGHpA vector cut with EcoRI+EcoRV. A plasmid map of pCMV-MIR101-1 is depicted in FIG. 3. A plasmid map of pAM_CBA-pl-WPRE-BGHpA is depicted in FIG. 4.

Figure 5:
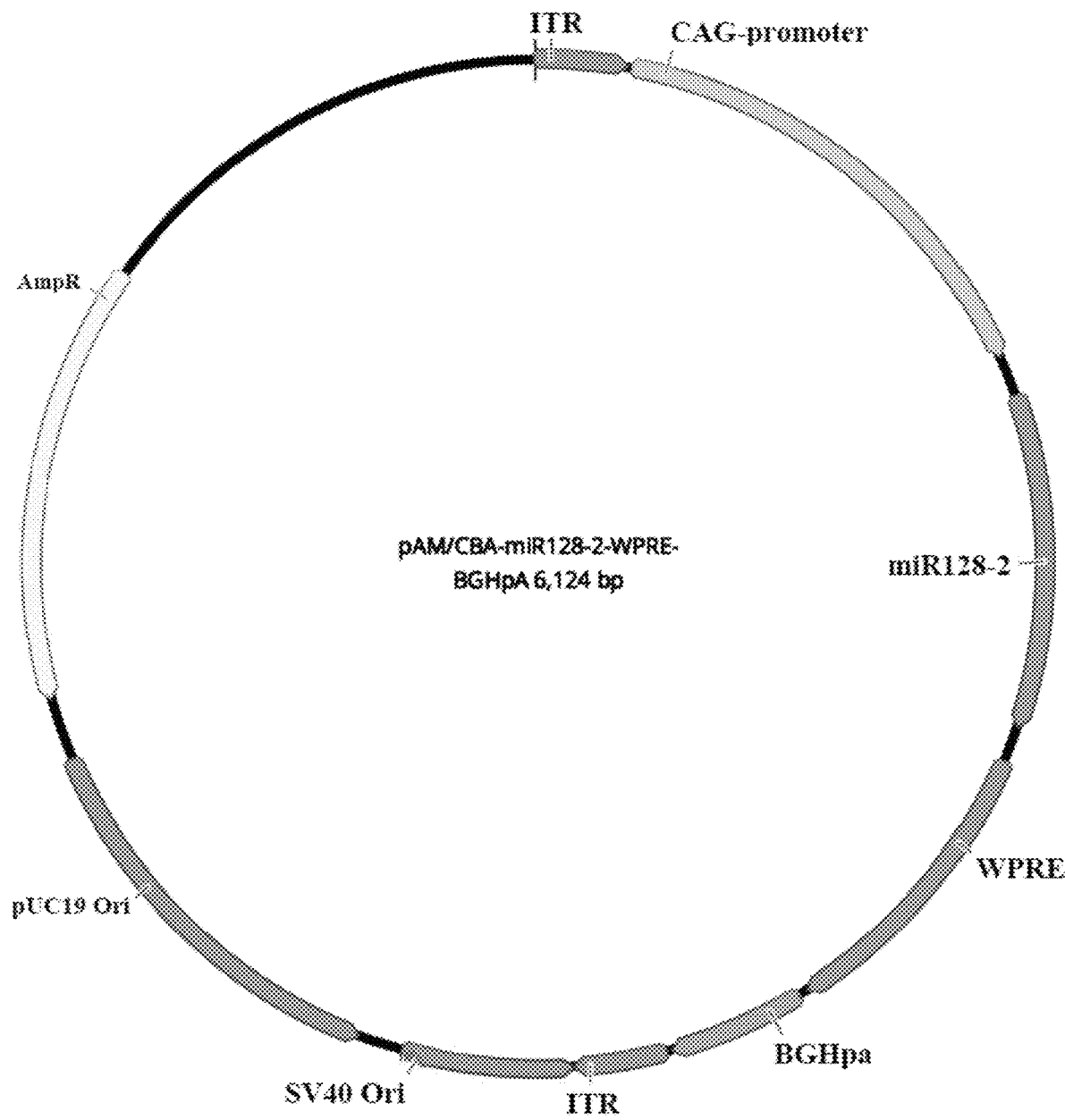
FIG. 5 is a plasmid map of pAM/CBA-miR128-2-WPRE-BGHpA.

In embodiments, the expression vector is pAM/CBA-miR128-2-WPRE-BGHpA. A plasmid map of pAM/CBA-miR128-2-WPRE-BGHpA is depicted in FIG. 5. The nucleic acid sequence [SEQ ID NO:4] is shown in FIGS. 6A-6D. TABLE II annotates pAM/CBA-miR128-2-WPRE-BGHpA.

TABLE II

| Name | Type | Minimum | Maximum | Length | Direction |
|---|---|---|---|---|---|
| Kan/Neo | CDS | 5072 | 5866 | 795 | reverse |
| IRES | regulatory | 4471 | 5056 | 586 | reverse |
| tGFP | CDS | 3772 | 4470 | 699 | reverse |
| ColE1 | rep_origin | 2680 | 3352 | 673 | forward |
| polyA | polyA_signal | 1819 | 2404 | 586 | forward |
| C | Editing History Deletion | 1027 | 1026 | 0 | none |
| miR128-2 | misc_feature | 1027 | 1678 | 652 | forward |
| CMV promoter | promoter uukaryotic | 200 | 926 | 727 | forward |

Figure 7:
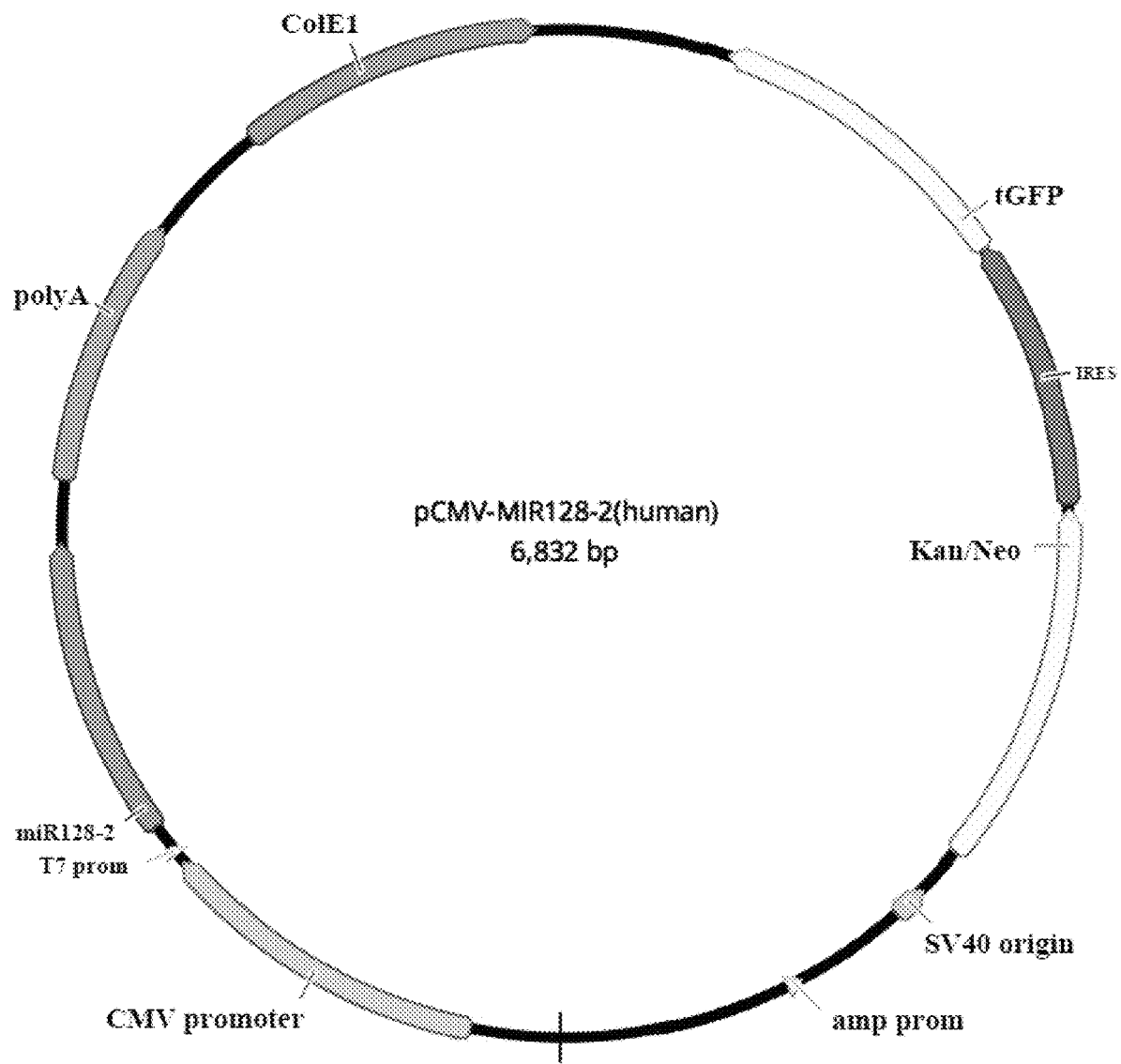
FIG. 7 is a plasmid map of pCMV-MIR128-2.

To construct pAM/CBA-miR128-2-WPRE-BGHpA, EcoRI-EcoRV fragments from the pCMV-MIR128-2 plasmid (755 bp) (SC400112), commercially available from OriGene Technologies, Inc., 9620 Medical Center Dr., Suite 200, Rockville, Md. 20850, is inserted into pAM_CBA-pl-WPRE-BGHpA vector cut with EcoRI+EcoRV. A plasmid map of pCMV-MIR128-2 is depicted in FIG. 7. A plasmid map of pAM_CBA-pl-WPRE-BGHpA is depicted in FIG. 4.

The microRNAs described herein, whether delivered by expression vector or by non-expression vector modalities, are used to treat seizure disorders. Seizure disorders, including those involving complex partial seizures, e.g., temporal lobe epilepsy (TLE) may be one of the most refractory forms of epilepsy. In certain instances, one temporal lobe may be defined as the site of seizure origin (the epileptogenic region) and the medial temporal lobe including the anterior hippocampus may be targeted in accordance with the methods herein. Seizure disorders can result from an imbalance of excitation to inhibition. The antagonism of excitation and enhancing of inhibition can provide improvement in at least one symptom of the seizure disorder.

Examples of seizure disorders include epilepsy, epilepsy with generalized tonic-clonic seizures, epilepsy with myoclonic absences, frontal lobe epilepsy, temporal lobe epilepsy, Landau-Kleffner Syndrome, Rasmussen's syndrome, Dravet syndrome, Doose syndrome, CDKL5 disorder, infantile spasms (West syndrome), juvenile myoclonic epilepsy (JME), vaccine-related encephalopathy, intractable childhood epilepsy (ICE), Lennox-Gastaut syndrome (LGS), Rett syndrome, Ohtahara syndrome, CDKL5 disorder, childhood absence epilepsy, essential tremor, acute repetitive seizures, benign rolandic epilepsy, status epilepticus, refractory status epilepticus, super-refractory status epilepticus (SRSE), PCDH19 pediatric epilepsy, drug withdrawal induced seizures, alcohol withdrawal induced seizures, increased seizure activity or breakthrough seizures (also called serial or cluster seizures). In embodiments, the seizure disorder is associated with a sodium channel protein type 1 subunit alpha (Scn1a)-related disorder. In embodiments, the seizure disorder is characterized by focal seizures. In embodiments, the seizure disorder is focal cortical dysplasia. In embodiments, the FCD is Type I FCD. In embodiments, the FCD is Type Ia FCD. In embodiments, the FCD is Type Ib FCD. In embodiments, the FCD is Type Ic FCD. In embodiments, the FCD is Type II FCD. In embodiments, the FCD is Type IIa FCD. In embodiments, the FCD is Type IIb FCD. In embodiments, the FCD is Type III FCD. In embodiments, the FCD is Type Ma FCD. In embodiments, the FCD is Type Mb FCD. In embodiments, the FCD is Type Mc FCD. In embodiments, the seizure disorder is associated with a brain tumor, i.e., brain tumor induced seizures, such as a ganglioglioma, a glioma—low grade and high grade, including anaplastic astrocytoma, anaplastic oligodendroglioma, anaplastic oligoastrocytoma, and anaplastic ependymoma, a glioblastoma, or a meningioma. In embodiments, the seizure disorder is associated with brain hamartomas, i.e., hamartoma induced seizures, such as Tuberous Sclerosis Complex (TSC) or Tuber Cinereum Hamartoma.

In embodiments, the seizure disorder is status epilepticus (SE). SE is characterized by an epileptic seizure of greater than five minutes or more than one seizure within a five-minute period without the person returning to normal between them. SE can be a dangerous condition that can lead to mortality if treatment is delayed. SE can be convulsive, with a regular pattern of contraction and extension of the arms and legs, or non-convulsive, with a change in a person's level of consciousness of relatively long duration but without large scale bending and extension of the limbs due to seizure activity. Convulsive SE (CSE) may be further classified into (a) tonic-clonic SE, (b) tonic SE, (c) clonic SE and (d) myoclonic SE. Non-convulsive SE (NCSE) is characterized by abnormal mental status, unresponsiveness, ocular motor abnormalities, persistent electrographic seizures, and possible response to anticonvulsants.

Symptoms of a seizure disorder may include, but are not limited to, episodes involving ataxia, gait impairment, speech impairment, vocalization, impaired cognition, abnormal motor activity, clinical seizure, subclinical seizure, hypotonia, hypertonia, drooling, mouthing behavior, aura, repetitive movements, laughing, and unusual sensations. In embodiments, the methods and compositions provided may reduce or prevent one or more different types of seizures. Generally, a seizure can include repetitive movements, unusual sensations, and combinations thereof. Seizures can be categorized as focal seizures (also referred to as partial seizures) and generalized seizures. Focal seizures affect only one side of the brain, while generalized seizures affect both sides of the brain. Specific types of focal seizures include simple focal seizures, complex focal seizures, and secondarily generalized seizures. Simple focal seizures can be restricted or focused on a particular lobe (e.g., temporal lobe, frontal lobe, parietal lobe, or occipital lobe). Complex focal seizures generally affect a larger part of one hemisphere than simple focal seizures, but commonly originate in the temporal lobe or the frontal lobe. When a focal seizure spreads from one side (hemisphere) to both sides of the brain, the seizure is referred to as a secondarily generalized seizure. Specific types of generalized seizures include absences (also referred to as petit mal seizures), tonic seizures, atonic seizures, myoclonic seizures, tonic clonic seizures (also referred to as grand mal seizures), and clonic seizures. Methods of treatment herein can include providing improvement in one or more of the foregoing symptoms.

Once a determination has been made of the location or of a suspected location of abnormal electrical impulses associated with a seizure disorder in a patient, targeted treatment in accordance with the present disclosure can be implemented. Methods of determining the location of abnormal electrical activity in the brain are well-known in the art. Although any area exhibiting abnormal electricity in the brain can be targeted for treatment herein, areas of the brain which are known to be associated with seizure disorders and which can receive targeted treatment include, but are not limited to, the temporal lobe, the frontal lobe, the occipital lobe and the parietal lobe. For example, the temporal lobes can be a common site of localized epileptic seizures. In certain instances, seizures beginning in the temporal lobes can extend to other parts of the brain. In embodiments, specific areas of the temporal lobe which can be targeted for treatment include structures of the limbic system such as the hippocampus, auditory-vestibular cortex, the medial temporal lobe, and the amygdala. In embodiments, specific areas of the occipital lobe can also be targeted, e.g., the primary visual cortex. In embodiments, specific areas of the parietal lobe can be targeted, e.g., the lateral postcentral gyms. In embodiments, the location of the primary somatosensory cortex which can be targeted. In embodiments, specific areas of the frontal lobe can be targeted, e.g., the motor cortex, the olfactory-gustatory cortex. In embodiments, large areas of the brain which have been identified as exhibiting abnormal electrical activity can be targeted. In certain instances, manifestations of seizure disorders can begin within certain areas of the brain and spread to others. For example, manifestations of seizure disorders can begin within the hippocampus or its surrounding structures. In embodiments, areas determined to be the site of origin of the abnormal electrical activity can be targeted.

Methods for administering materials directly to target locations within the brain are well-known. For example, a hole, e.g., Burr hole, can be drilled into the skull and an appropriately sized needle may be used to deliver a vector or non-vector vehicle to a target location. In embodiments, a portion of the skull may be removed to expose the dura matter (craniotomy) at or near a target location and a vector or non-vector vehicle can be administered directly to the target location. In embodiments, a vector or non-vector vehicle is injected intracranially using stereotaxic coordinates, a micropipette and an automated pump for precise delivery of the vector or non-vector vehicle to the desired area with minimal damage to the surrounding tissue. In embodiments, a micropump may be utilized to deliver pharmaceutical compositions containing a vector or non-vector vehicle containing the microRNA(s) to target areas in the brain. The compositions can be delivered immediately or over an extended period of time, e.g., over 1, 2, 3, 4, 5, 6, 7, 8, 9, 10 or more minutes. After vector delivery to a target location in the brain a sufficient amount of time may be allowed to pass to allow expression of the microRNA(s) at the target location.

In embodiments, vectors or nonvector delivery vehicles herein can be administered systemically. Systemic delivery includes oral, buccal, sublingual, rectal, topical, intranasal, vaginal and parenteral modes of administration. Examples of parenteral modes of administration include intravenous, intraperitoneal, intramuscular and subcutaneous modes of administration. In embodiments, vectors or nonvector delivery vehicles will circulate until they contact the target location(s) in the brain where they deliver the microRNA(s) or cause the microRNA(s) to be expressed and act, e.g., to aid in network formation and/or modulate neuronal signaling networks.

The microRNA(s) is used in an amount effective against a seizure disorder in patients. The dosage of the active ingredient depends upon the age, weight, and individual condition of the patient, the individual pharmacokinetic data, and the mode of administration. In the case of an individual human having a bodyweight of about 70 kg the daily dose administered of a microRNA can be from 0.01 mg/kg bodyweight to 100 mg/kg bodyweight, e.g., from 0.1 mg/kg bodyweight to 50 mg/kg bodyweight, from 1 mg/kg to 20 mg/kg bodyweight administered as a single dose or as several doses. The microRNA(s) can be used alone or in combination with other AED drugs.

In embodiments, treatment with ultrasound is used to enhance delivery of the microRNA(s) to target locations in the brain by disrupting the blood brain barrier. Use of focused ultrasound energy herein disrupts the BBB without adversely affecting the vector, non-vector delivery vehicle, the microRNA(s), and/or brain tissue itself. This may be considered surprising in view of potential damage to organic compounds and tissues by ultrasound energy. Use of ultrasound energy herein can increase the speed of delivery of vectors, non-vector delivery vehicles, and/or the microRNA(s) to target locations in the brain, reduce side effects which may be associated with delivery of vectors non-vector delivery vehicles, and/or the microRNA(s) to target locations in the brain, reduce dosage amounts while concentrating vectors, non-vector delivery vehicles, and/or the microRNA(s) at a target location and can allow controlled release of the amount of vectors, non-vector delivery vehicles, and/or the microRNA(s) at a target location.

In accordance with the present disclosure, in embodiments, ultrasound energy assists and/or propels penetration of the vector carrying the microRNA(s) to target locations in the brain. In embodiments, ultrasound energy is used to make the blood brain barrier permeable to vectors, non-vector delivery vehicles, and/or the microRNA(s) herein. Accordingly, in embodiments, ultrasound energy can be applied to a target location prior to administration of the vector, non-vector delivery vehicles, and/or the microRNA(s). In embodiments, vectors, non-vector delivery vehicles, and/or the microRNA(s) herein can be administered to a target area in the brain simultaneously with administration of ultrasound energy. In embodiments, vectors, non-vector delivery vehicles, and/or the microRNA(s), herein can be administered to a target area in the brain before administration of ultrasound energy.

As mentioned previously, vectors, non-vector delivery vehicles, and/or the microRNA(s) herein can be administered systemically. In this manner vectors, non-vector delivery vehicles, and/or the microRNA(s) circulating in the blood stream are delivered to a target location in the brain through a portion of the BBB disrupted by ultrasonic energy. In embodiments, vectors, non-vector delivery vehicles, and/or the microRNA(s) herein can be administered systemically after ultrasound energy treatment of the target location and the vectors, non-vector delivery vehicles, and/or the microRNA(s) penetrate the disrupted BBB to become situated at the target location. In embodiments, vectors, non-vector delivery vehicles, and/or the microRNA(s), herein can be administered directly to a target location in the brain. In embodiments, vectors, non-vector delivery vehicles, and/or the microRNA(s) herein can be administered directly to a target location in the brain after ultrasound energy treatment of the target location to become situated at the target location. In embodiments, vectors, non-vector delivery vehicles, and/or the microRNA(s) herein can be administered directly to a target location in the brain without ultrasound treatment.

In embodiments, ultrasound energy can be administered to a target area by removing a portion of the skull (craniotomy) to expose the dura matter at or near a target location and delivering the ultrasound energy at or below the exposed dura matter. In embodiments, ultrasound energy can be administered to a target location through the skull, eliminating the need for surgery associated with delivery of ultrasound energy to a target location. Methods for delivering ultrasound energy through the skull are known in the art. See, e.g., U.S. Pat. No. 5,752,515 and US Publication No. 2009/0005711, both of which are hereby incorporated by reference in their respective entireties. See also, Hynynen et al., NeuroImage 24 (2005) 12-120.

In embodiments, ultrasound energy can be applied to a target location in the brain at frequencies ranging from about 20 kHz to about 5 MHz, and with sonication duration ranging from 100 nanoseconds to 1 minute. In embodiments, ultrasound energy can be applied to a target location in the brain at frequencies ranging from about 20 kHz to about 10 MHz, sonication duration ranging from about 100 nanoseconds to about 30 minutes, with continuous wave or burst mode operation, where the burst mode repetition varies from about 0.01 Hz to about 1 MHz. In embodiments, ultrasound energy can be applied to a target location in the brain at frequencies ranging from about 200 kHz to about 10 MHz, and with sonication duration ranging from about 100 milliseconds to about 30 minutes. In embodiments, ultrasound energy can be applied to a target location in the brain at frequencies ranging from about 250 kHz to about 10 MHz, and with sonication duration ranging from about 0.10 microseconds to about 30 minutes. In embodiments, ultrasound energy can be applied to a target location in the brain at a frequency of about 1.525 MHz. In embodiments, ultrasound energy can be applied to a target location in the brain at a frequency of about 0.69 MHz. In embodiments, pressure amplitudes generated by ultrasound energy can be about 0.5 to about 2.7 MPa. In embodiments, pressure amplitudes generated by ultrasound energy can be about 0.8 to about 1 MPa. In embodiments, ultrasound energy is applied to a target location in the brain at a focal region sized in accord with the volume of tissue and/or fluids to which a vector, non-vector delivery vehicle, and/or the microRNA(s) herein is to be delivered, e.g., from about 0.1 mm$^3$ to about 5 cm$^3$.

In embodiments, the target location and access thereto is confirmed by introducing a contrast agent into the patient prior to, during or after application of ultrasound energy to the target location, allowing sufficient time for the contrast agent to permeate the BBB, and determining whether the contrast agent is present at the target location. Contrast agents are well-known and include, e.g., iodine-based compounds, barium-based compounds and lanthanide based compounds. Iodine-based agents include, e.g., iohexol, iopromide, iodixanol, iosimenol, ioxaglate, iothalamate and iopamidol. Barium-based compounds include barium sulfate. Lanthanide-based compounds include, e.g., gadolinium-based chelates such as gadoversetamide, gadopentetate dimeglumine, gadobutrol, gadobenate dimeglumine, gadoterate meglumine, and gadoxetate disodium. Detection modalities include 2-dimensional X-ray radiography, X-ray computed tomography and magnetic resonance imaging which are well-known techniques that may be utilized to confirm the presence or absence of contrast agent in a target location.

In accordance with the present disclosure, microRNA treatment provides improvement in one or more symptoms of a seizure disorder for more than 1 hour after administration to the patient. In embodiments, microRNA treatment provides improvement in one or more symptoms of the disorder for more than 2 hours after administration to the patient. In embodiments, microRNA treatment provides improvement in one or more symptoms of the disorder for more than 3 hours after administration to the patient. In embodiments, microRNA treatment provides improvement in one or more symptoms of the disorder for more than 4 hours after administration to the patient. In embodiments, microRNA treatment provides improvement in one or more symptoms of the disorder for more than 6 hours after administration to the patient. In embodiments, microRNA treatment provides improvement in one or more symptoms of the disorder for more than 8, 10, 12, 14, 16, 18, 20, 22 or 24 hours after administration to the patient. In embodiments, improvement in at least one symptom for 12 hours after administration to the patient is provided in accordance with the present disclosure. In embodiments, microRNA treatment provides improvement of next day functioning of the patient. For example, the microRNA may provide improvement in one or more symptoms of the disorder for more than about, e.g., 2 hours, 4 hours, 6 hours, 8 hours, 10 hours, 12 hours, 14 hours, 16 hours, 18 hours, 20 hours, 22 hours or 24 hours after administration and waking from a night of sleep.

In embodiments, provided herein are methods of treating a seizure disorder including administering to a patient in need thereof microRNA(s) after a warning sign of an impending seizure is detected to reduce or prevent seizure activity.

In embodiments, the methods described herein are effective to reduce, delay, or prevent one or more other clinical symptoms of a seizure disorder. For example, the effect, in a patient of microRNA treatment in a target location of the brain, whose delivery is optionally enhanced by ultrasound energy on a particular symptom, pharmacologic, or physiologic indicator can be compared to an untreated patient, or the condition of the patient prior to treatment. In embodiments, the symptom, pharmacologic, and/or physiologic indicator is measured in a patient prior to treatment, and again one or more times after treatment is initiated. In embodiments, the control is a reference level, or average determined based on measuring the symptom, pharmacologic, or physiologic indicator in one or more patients that do not have the disease or condition to be treated (e.g., healthy patients). In embodiments, the amount of miR-101 and/or miR-128 in brain tissue prior to treatment is compared to the amount of miR-101 and/or miR-128 in brain tissue after treatment. In embodiments, the effect of the treatment is compared to a conventional treatment that is within the purview of those skilled in the art.

Effective treatment of a seizure disorder (e.g., intractable focal seizures, focal cortical dysplasia, acute repetitive seizure, status epilepticus, etc.) herein may be established by showing reduction in the frequency or severity of symptoms (e.g., more than 10%, 20%, 30% 40% or 50%) after a period of time compared with baseline. For example, after a baseline period of 1 month, the patients having microRNA treatment may be randomly allocated a placebo as add-on therapy to standard therapies, during a double-blind period of 2 months. Primary outcome measurements may include the percentage of responders on a microRNA and on placebo, defined as having experienced at least a 10% to 50% reduction of symptoms during the second month of the double-blind period compared with baseline.

In embodiments, pharmaceutical compositions containing vectors, non-vector delivery vehicles, and/or the microRNA(s) may be provided with conventional release or modified release profiles. Pharmaceutical compositions may be prepared using a pharmaceutically acceptable "carrier" composed of materials that are considered safe and effective. The "carrier" includes all components present in the pharmaceutical formulation other than the active substance or ingredients. Examples of active substances include microRNA(s), expression vectors containing microRNA(s) and AEDs. The term "carrier" includes, but is not limited to, diluents, binders, lubricants, disintegrants, fillers, and coating compositions. Those with skill in the art are familiar with such pharmaceutical carriers and methods of compounding pharmaceutical compositions using such carriers.

In embodiments, pharmaceutical compositions containing vectors, non-vector delivery vehicles, and/or the microRNA(s) are suitable for parenteral administration, including, e.g., intramuscular (i.m.), intravenous (i.v.), subcutaneous (s.c.), intraperitoneal (i.p.), or intrathecal (i.t.). Parenteral compositions must be sterile for administration by injection, infusion or implantation into the body and may be packaged in either single-dose or multi-dose containers. In embodiments, liquid pharmaceutical compositions for parenteral administration to a patient include an active substance, e.g., vectors, non-vector delivery vehicles, and/or the microRNA(s), in any of the respective amounts described above. In embodiments, the pharmaceutical compositions for parenteral administration are formulated as a total volume of about, e.g., 0.1 ml, 0.25 ml, 0.5 ml, 0.75 ml, 1 ml, 1.25 ml, 1.5 ml, 1.75 ml, 2 ml, 2.25 ml, 2.5 ml, 2.75 ml, 3 ml, 3.25 ml, 3.5 ml, 3.75 ml, 4 ml, 4.25 ml, 4.5 ml, 4.75 ml, 5 ml, 10 ml, 20 ml, 25 ml, 50 ml, 100 ml, 200 ml, 250 ml, or 500 ml. In embodiments, the volume of pharmaceutical compositions containing expression vectors are microliter amounts. For example, 0.1 microliters to 10 or more microliters can be injected. For example, 0.1, 0.2, 0.3, 0.4, 0.5, 0.6, 0.7, 0.8, 0.9, 1.0, 1.25, 1.5, 1.75, 2.0, 2.25, 2.5, 2.75, 3.0, 3.25, 3.5, 3.75, 4.0, 4.25, 4.5, 4.75, 5.0, 5.25, 5.5, 5.75, 6.0, 6.25, 6.5, 6.75, 7.0, 8.25, 8.5, 8.75, 9.0, 9.25, 9.5, 9.75, or 10 microliters. In embodiments, the compositions are contained in a micropipette, a bag, a glass vial, a plastic vial, or a bottle.

In embodiments, pharmaceutical compositions for parenteral administration include respective amounts described above. In embodiments, pharmaceutical compositions for parenteral administration include about 0.0001 mg to about 500 mg active substance, e.g., vectors, non-vector delivery vehicles, and/or the microRNA(s). In embodiments, pharmaceutical compositions for parenteral administration to a patient include an active substance, e.g., vectors, non-vector delivery vehicles, and/or the microRNA(s), at a respective concentration of about 0.001 mg/ml to about 500 mg/ml. In embodiments, the pharmaceutical composition for parenteral administration includes an active substance at a respective concentration of, e.g., about 0.005 mg/ml to about 50 mg/ml, about 0.01 mg/ml to about 50 mg/ml, about 0.1 mg/ml to about 10 mg/ml, about 0.05 mg/ml to about 25 mg/ml, about 0.05 mg/ml to about 10 mg/ml, about 0.05 mg/ml to about 5 mg/ml, or about 0.05 mg/ml to about 1 mg/ml. In embodiments, the pharmaceutical composition for parenteral administration includes an active substance at a respective concentration of, e.g., about 0.05 mg/ml to about 15 mg/ml, about 0.5 mg/ml to about 10 mg/ml, about 0.25 mg/ml to about 5 mg/ml, about 0.5 mg/ml to about 7 mg/ml, about 1 mg/ml to about 10 mg/ml, about 5 mg/ml to about 10 mg/ml, or about 5 mg/ml to about 15 mg/ml.

In embodiments, a pharmaceutical composition for parenteral administration is provided wherein the pharmaceutical composition is stable for at least six months. In embodiments, the pharmaceutical compositions for parenteral administration exhibit no more than about 5% decrease in active substance for at least, e.g., 3 months or 6 months. In embodiments, the amount of vector or non-vector vehicle, degrades at no more than about, e.g., 2.5%, 1%, 0.5% or 0.1%. In embodiments, the degradation is less than about, e.g., 5%, 2.5%, 1%, 0.5%, 0.25%, 0.1%, for at least six months.

In embodiments, pharmaceutical compositions for parenteral administration are provided wherein the pharmaceutical composition remains soluble. In embodiments, pharmaceutical compositions for parenteral administration are provided that are stable, soluble, local site compatible and/or ready-to-use. In embodiments, the pharmaceutical compositions herein are ready-to-use for direct administration to a patient in need thereof.

The pharmaceutical compositions for parenteral administration provided herein may include one or more excipients, e.g., solvents, solubility enhancers; suspending agents, buffering agents, isotonicity agents, stabilizers or antimicrobial preservatives. When used, the excipients of the parenteral compositions will not adversely affect the stability, bioavailability, safety, and/or efficacy of a vector, non-vector delivery vehicle, and/or the microRNA(s), used in the composition. Thus, parenteral compositions are provided wherein there is no incompatibility between any of the components of the dosage form.

In embodiments, parenteral compositions including vectors, non-vector delivery vehicles, and/or the microRNA(s) include a stabilizing amount of at least one excipient. For example, excipients may be selected from the group consisting of buffering agents, solubilizing agents, tonicity agents, antioxidants, chelating agents, antimicrobial agents, and preservative. One skilled in the art will appreciate that an excipient may have more than one function and be classified in one or more defined group.

In embodiments, parenteral compositions include a vector, non-vector delivery vehicle, and/or the microRNA(s) and an excipient wherein the excipient is present at a weight percent (w/v) of less than about, e.g., 10%, 5%, 2.5%, 1%, or 0.5%. In embodiments, the excipient is present at a weight percent between about, e.g., 1.0% to 10%, 10% to 25%, 15% to 35%, 0.5% to 5%, 0.001% to 1%, 0.01% to 1%, 0.1% to 1%, or 0.5% to 1%. In embodiments, the excipient is present at a weight percent between about, e.g., 0.001% to 1%, 0.01% to 1%, 1.0% to 5%, 10% to 15%, or 1% to 15%.

In embodiments, parenteral compositions may be administered as needed, e.g., once, twice, three, four, five, six or more times daily, or continuously depending on the patient's needs.

In embodiments, parenteral compositions of an active substance are provided, wherein the pH of the composition is between about 4.0 to about 8.0. In embodiments, the pH of the compositions is between, e.g., about 5.0 to about 8.0, about 6.0 to about 8.0, about 6.5 to about 8.0. In embodiments, the pH of the compositions is between, e.g., about 6.5 to about 7.5, about 7.0 to about 7.8, about 7.2 to about 7.8, or about 7.3 to about 7.6. In embodiments, the pH of the aqueous solution is, e.g., about 6.8, about 7.0, about 7.2, about 7.4, about 7.6, about 7.7, about 7.8, about 8.0, about 8.2, about 8.4, or about 8.6.

Unless defined otherwise, all technical and scientific terms used herein have the same meanings as commonly understood by one of skill in the art to which the disclosure herein belongs.

The term "about" or "approximately" as used herein means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, up to 10%, up to 5%, and/or up to 1% of a given value. Alternatively, particularly with respect to biological systems or processes, the term can mean within an order of magnitude, preferably within 5-fold, and more preferably within 2-fold, of a value.

"Improvement" refers to the treatment of seizure disorders such as focal epilepsy, intractable focal epilepsy, focal cortical dysplasia, epilepsy, epilepsy with generalized tonic-clonic seizures, epilepsy with myoclonic absences, frontal lobe epilepsy, temporal lobe epilepsy, Landau-Kleffner Syndrome, Rasmussen's syndrome, Dravet syndrome, Doose syndrome, CDKL5 disorder, infantile spasms (West syndrome), juvenile myoclonic epilepsy (JME), vaccine-related encephalopathy, intractable childhood epilepsy (ICE), Lennox-Gastaut syndrome (LGS), Rett syndrome, Ohtahara syndrome, CDKL5 disorder, childhood absence epilepsy, essential tremor, acute repetitive seizures, benign rolandic epilepsy, status epilepticus, refractory status epilepticus, super-refractory status epilepticus (SRSE), PCDH19 pediatric epilepsy, brain tumor induced seizures, hamartoma induced seizures, drug withdrawal induced seizures, alcohol withdrawal induced seizures, increased seizure activity or breakthrough seizures (also called serial or cluster seizures), measured relative to at least one symptom of the foregoing disorders.

"Improvement in next day functioning" or "wherein there is improvement in next day functioning" refers to improvement after waking from an overnight sleep period wherein the beneficial effect of administration of microRNA therapy to a patient applies to at least one symptom of a syndrome or disorder herein and is discernable, either subjectively by a patient or objectively by an observer, for a period of time, e.g., 2 hours, 3 hours, 4 hours, 5 hours, 6 hours, 12 hours, 24 hours, etc. after waking.

"Treating", "treatment" or "treat" can refer to the following: alleviating or delaying the appearance of clinical symptoms of a disease or condition in a patient that may be afflicted with or predisposed to the disease or condition, but does not yet experience or display clinical or subclinical symptoms of the disease or condition. In certain embodiments, "treating", "treat" or "treatment" may refer to preventing the appearance of clinical symptoms of a disease or condition in a patient that may be afflicted with or predisposed to the disease or condition, but does not yet experience or display clinical or subclinical symptoms of the disease or condition. "Treating", "treat" or "treatment" also refers to inhibiting the disease or condition, e.g., arresting or reducing its development or at least one clinical or subclinical symptom thereof. "Treating", "treat" or "treatment" further refers to relieving the disease or condition, e.g., causing regression of the disease or condition or at least one of its clinical or subclinical symptoms. The benefit to a patient to be treated may be statistically significant, mathematically significant, or at least perceptible to the patient and/or the physician. Nonetheless, prophylactic (preventive) treatment and therapeutic (curative) treatment are two separate embodiments of the disclosure herein.

"Pharmaceutically acceptable" refers to molecular entities and compositions that are "generally regarded as safe", e.g., that are physiologically tolerable and do not typically produce an allergic or similar untoward reaction, such as gastric upset and the like, when administered to a human. In embodiments, this term refers to molecular entities and compositions approved by a regulatory agency of the federal or a state government, as the GRAS list under section 204(s) and 409 of the Federal Food, Drug and Cosmetic Act, that is subject to premarket review and approval by the FDA or similar lists, the U.S. Pharmacopeia or another generally recognized pharmacopeia for use in animals, and more particularly in humans.

"Effective amount" or "therapeutically effective amount" can mean a dosage sufficient to alleviate one or more symptoms of a syndrome, disorder, disease, or condition being treated, or to otherwise provide a desired pharmacological and/or physiologic effect. "Effective amount" or "therapeutically effective amount" may be used interchangeably herein.

"Co-administered with", "administered in combination with", "a combination of" or "administered along with" may be used interchangeably and mean that two or more agents are administered in the course of therapy. The agents may be administered together at the same time or separately in spaced apart intervals. The agents may be administered in a single dosage form or in separate dosage forms.

"Patient in need thereof" may include individuals, e.g., mammals such as humans, canines, felines, porcines, rodents, etc., that have been diagnosed with a seizure disorder such as epilepsy, epilepsy with generalized tonic-clonic seizures, epilepsy with myoclonic absences, focal epilepsy, intractable focal epilepsy, focal cortical dysplasia, frontal lobe epilepsy, temporal lobe epilepsy, Landau-Kleffner Syndrome, Rasmussen's syndrome, Dravet syndrome, Doose syndrome, CDKL5 disorder, infantile spasms (West syndrome), juvenile myoclonic epilepsy (JME), vaccine-related encephalopathy, intractable childhood epilepsy (ICE), Lennox-Gastaut syndrome (LGS), Rett syndrome, Ohtahara syndrome, CDKL5 disorder, childhood absence epilepsy, essential tremor, acute repetitive seizures, benign rolandic epilepsy, status epilepticus, refractory status epilepticus, super-refractory status epilepticus (SRSE), PCDH19 pediatric epilepsy, brain tumor induced seizures, hamartoma induced seizures, drug withdrawal induced seizures, alcohol withdrawal induced seizures, increased seizure activity or breakthrough seizures (also called serial or cluster seizures). Seizure disorders can be associated with a sodium channel protein type 1 subunit alpha (Scn1a)-related disorder. The methods may be provided to any individual including, e.g., wherein the patient is a neonate, infant, a pediatric patient (6 months to 12 years), an adolescent patient (age 12-18 years) or an adult (over 18 years). Patients include mammals.

"Prodrug" refers to a pharmacological substance (drug) that is administered to a patient in an inactive (or significantly less active) form. Once administered, the prodrug is metabolized in the body (in vivo) into a compound having the desired pharmacological activity.

"Analog" and "Derivative" may be used interchangeably and refer to a compound that possesses the same core as the parent compound, but may differ from the parent compound in bond order, the absence or presence of one or more atoms and/or groups of atoms, and combinations thereof. Enantiomers are examples of derivatives. The derivative can differ from the parent compound, for example, in one or more substituents present on the core, which may include one or more atoms, functional groups, or substructures. In general, a derivative can be imagined to be formed, at least theoretically, from the parent compound via chemical and/or physical processes.

The term "pharmaceutically acceptable salt", as used herein, refers to derivatives of the compounds defined herein, wherein the parent compound is modified by making acid or base salts thereof. Examples of pharmaceutically acceptable salts include, but are not limited to, nontoxic base addition salts with inorganic bases. Suitable inorganic bases such as alkali and alkaline earth metal bases include metallic cations such as sodium, potassium, magnesium, calcium and the like. The pharmaceutically acceptable salts can be synthesized from the parent compound by conventional chemical methods.

EXAMPLES

The examples provided herein are included solely for augmenting the disclosure herein and should not be considered to be limiting in any respect.

Example I

Hu-pri-miR sequences as described below are cloned into a AAV pAM-plasmid backbone. Each plasmid will be verified by sequencing and restriction digests.
1. pAM-CBA-hu-pri-miR128-2-WPRE-bGH
2. pAM-CBA-hu-pri-miR101-WPRE-bGH
3. pAM-CBA-sc-hu-pri-miR128-2-GFP-WPRE-bGH Plasmids expressing a GFP reporter facilitate analysis of in vivo spread of miR expression following infusion into the mouse brain.

Plasmids 1-3 above and pAM-empty plasmid will be packaged into AAVRec3 vectors (~300 µL AAV vector; >1×10$^{12}$ vg/mL) and purified using standard iodixanol purification methods. AAV vector stock purity will be confirmed by standard SDS-PAGE and Coomassie staining methods. AAV vector titers will be determined by quantitative RT-PCR.

Study 1: Optimization of AAV Vector Dose

AAV miR-128-2-GFP and AAV miR128-2 vector will be injected into the mouse brain at two vector doses (n=4 animals per vector and at 2 doses) (miR128-2 only vector included in the event there are synergistic toxic effects with GFP). Brains will be taken at 4 weeks post-vector infusion for analysis of transgene expression (for GFP) and spread and any evidence of toxicity (GFAP, Cd11b, NeuN IHC, Fluorojade) using standardized lab methods.

Study 2: Optimization of AAV Vector Dose

AAV miR-101-1-GFP and AAV miR101-1 vector will be injected into the mouse brain at two vector doses (n=4 animals per vector and at 2 doses) (miR101-1 only vector included in the event there are synergistic toxic effects with GFP). Brains will be taken at 4 weeks post-vector infusion for analysis of transgene expression (for GFP) and spread and any evidence of toxicity (GFAP, Cd11b, NeuN IHC, Fluorojade) using standardized lab methods.

Study 3:

The following treatment groups will be generated. Brains will be taken at 3-4 weeks post-vector infusion for analyses.

Treatment Groups:
AAV-miR128-2
AAV-miR101
AAV-miR128-2/miR101
Animal group sizes: n=8 per vector.
Analyses:
  Toxicity—NeuN IHC, Fluorojade staining.
  Effect on expression of target gene expression determined by RT-qPCR/digital drop PCR. Western blot and/or IHC methods will be performed where possible if antibodies to these targets are available.
    miR-128-2 targets
      slc6al (EAAT3), TARPP, Pea15a, ERK1/2 activation—striatal samples.
    miR-101 targets
      NKCC1, Ank2, Kif1a (presynaptic), Abca1, Ndrg2 (glial), xCT, PMCA2

Example 2

Prospective Assessment of Efficacy of MicroRNA Treatment in Mouse Seizure Model

On day one, 50 mice will be injected with kainic acid (KA, 200 ng/nl) in the hippocampus under isoflurane anesthesia. On day 21, AAVRec3-pAM/CBA-miR101-1-WPRE-BGHpA (4.66 E+13 genome copies/ml) will be injected in the sclerotic hippocampus (500 nl). In 25 IHKA control mice AAVRec3-pAM_CBA-pl-WPRE-BGHpA control vector will be injected. At the same time a bipolar recording electrode will be implanted in the hippocampus. On days 25, 27, 30, 32 and 35, mice will be selected for evaluation. About 20% to 25% of the animals (5 to 6 mice/group) will be examined. EEG will continuously be recorded and recorded signals will be further processed to quantify the number of seizures. Mice will be evaluated to determine which dosages provide prolonged seizure suppression without side effects. An endpoint is at least 8 hours seizure suppression.

Example 3

Prospective Assessment of Efficacy of MicroRNA Treatment in Mouse Seizure Model

On day one, 50 mice will be injected with kainic acid (KA, 200 ng/nl) in the hippocampus under isoflurane anesthesia. On day 21, AAVRec3-pAM/CBA-miR128-2-WPRE-BGHpA (4.66 E+13 genome copies/ml) will be injected in the sclerotic hippocampus (500 nl). In 25 IHKA control mice AAVRec3-pAM_CBA-pl-WPRE-BGHpA control vector will be injected. At the same time a bipolar recording electrode will be implanted in the hippocampus. On days 25, 27, 30, 32 and 35, mice will be selected for evaluation. About 20% to 25% of the animals (5 to 6 mice/group) will be examined. EEG will continuously be recorded and recorded signals will be further processed to quantify the number of seizures. Mice will be evaluated to determine which dosages provide prolonged seizure suppression without side effects. An endpoint is at least 8 hours seizure suppression.

Example 4

Prospective Assessment of Efficacy of Ultrasound Enhanced MicroRNA Treatment in Mouse Seizure Model On day one, 50 mice will be injected with kainic acid (KA, 200 ng/nl) in the hippocampus under 2% isoflurane anesthesia. On day 21, AAVRec3-pAM/CBA-miR101-1-WPRE-BGHpA (4.66 E+13 genome copies/ml) will be injected in the sclerotic hippocampus (500 nl). In 25 IHKA control mice AAVRec3-pAM_CBA-pl-WPRE-BGHpA control vector will be injected.

Prior to AAVRec3-pAM/CBA-miR101-1-WPRE-BGHpA administration, ultrasound energy will be applied to the BBB proximate to the hippocampal locus of the modified receptors. Each mouse will be anesthetized using 2% isoflurane and placed prone with its head immobilized by a stereotaxic apparatus that includes a mouse head holder, ear bars, and a gas anesthesia mask. The mouse hair will be removed using an electric trimmer and a depilatory cream. A degassed water-filled container sealed at the bottom with a thin, acoustically and optically transparent plastic wrap will be placed on top of the mouse head. Ultrasound coupling gel will also be used to eliminate any remaining impedance mismatch.

Ultrasound waves will be generated by a single-element spherical segment focused ultrasound transducer (center frequency: 1.525 MHz, focal depth: 90 mm, radius: 30 mm, available, e.g., from Riverside Research Institute, New York, N.Y., USA). A pulse-echo diagnostic transducer (center frequency: 7.5 MHz, focal length: 60 mm) will be aligned through a central, circular hole (radius 11.2 mm) of the focused ultrasound transducer so that the foci of the two transducers fully overlap. A cone filled with degassed and distilled water will be mounted onto the transducer system with the water contained in the cone by an acoustically transparent polyurethane membrane cap. The transducer system will be attached to a computer-controlled, three-dimensional positioning system (e.g., available from Velmex Inc., Lachine, QC, CAN). The focused ultrasound transducer will be connected to a matching circuit and driven by a computer-controlled function generator and a 50-dB power amplifier. The pulse-echo transducer will be driven by a pulser-receiver system connected to a digitizer in a personal computer.

The focused ultrasound transducer will be submerged in the degassed water-filled container with its beam axis perpendicular to the surface of the skull. The focus of the transducer will be positioned inside the mouse brain using, e.g., a grid-positioning method. The beam axis of the transducer will be aligned such that the focal point is placed 3 mm beneath the top of the parietal bone of the skull. In this placement, the focus of the focused ultrasound beam will overlap with the left hippocampus and the left posterior cerebral artery (PCA). The right hippocampus will not be targeted and can be used as a control.

A 25 µl bolus of ultrasound contrast agents constituting of microbubbles (mean diameter: 3.0-4.5 µm, concentration: $5.0\text{-}8.0\times10^8$ bubbles per ml) will be injected into the tail vein 1-4 minutes prior to sonication. Pulsed focused ultrasound (pulse rate: 10 Hz, pulse duration: 20 ms, duty cycle: 20%) will then be applied at 0.64 MPa peak-to-peak in a series of two bursts consisting of 30 s of sonication at a single location (i.e., the hippocampus). Between each burst, a 30-s interval will be allowed for any residual heat between pulses to dissipate. The focused ultrasound sonication procedure can be performed one or more times in each mouse brain.

Following BBB opening, a bipolar recording electrode will be implanted in the hippocampus. Mice will be evaluated to determine which dosages provide prolonged seizure suppression without side effects. An endpoint is at least 8 hours seizure suppression.

Example 5

Prospective Assessment of Efficacy of Ultrasound Enhanced MicroRNA Treatment in Mouse Seizure Model On day one, 50 mice will be injected with kainic acid (KA, 200 ng/nl) in the hippocampus under 2% isoflurane anesthesia. On day 21, AAVRec3-pAM/CBA-miR128-2-WPRE-BGHpA (4.66 E+13 genome copies/ml) will be injected in the sclerotic hippocampus (500 nl). In 25 IHKA control mice AAVRec3-pAM_CBA-pl-WPRE-BGHpA control vector will be injected.

Prior to AAVRec3-pAM/CBA-miR128-2-WPRE-BGHpA administration, ultrasound energy will be applied to the BBB proximate to the hippocampal locus of the modified receptors. Each mouse will be anesthetized using 2% isoflurane and placed prone with its head immobilized by a stereotaxic apparatus that includes a mouse head holder, ear bars, and a gas anesthesia mask. The mouse hair will be removed using an electric trimmer and a depilatory cream. A degassed water-filled container sealed at the bottom with a thin, acoustically and optically transparent plastic wrap will be placed on top of the mouse head. Ultrasound coupling gel will also be used to eliminate any remaining impedance mismatch.

Ultrasound waves will be generated by a single-element spherical segment focused ultrasound transducer (center frequency: 1.525 MHz, focal depth: 90 mm, radius: 30 mm, available, e.g., from Riverside Research Institute, New York, N.Y., USA). A pulse-echo diagnostic transducer (center frequency: 7.5 MHz, focal length: 60 mm) will be aligned through a central, circular hole (radius 11.2 mm) of the focused ultrasound transducer so that the foci of the two transducers fully overlap. A cone filled with degassed and distilled water will be mounted onto the transducer system with the water contained in the cone by an acoustically transparent polyurethane membrane cap. The transducer system will be attached to a computer-controlled, three-dimensional positioning system (e.g., available from Velmex Inc., Lachine, QC, CAN). The focused ultrasound transducer will be connected to a matching circuit and driven by a computer-controlled function generator and a 50-dB power amplifier. The pulse-echo transducer will be driven by a pulser-receiver system connected to a digitizer in a personal computer.

The focused ultrasound transducer will be submerged in the degassed water-filled container with its beam axis perpendicular to the surface of the skull. The focus of the transducer will be positioned inside the mouse brain using, e.g., a grid-positioning method. The beam axis of the transducer will be aligned such that the focal point is placed 3 mm beneath the top of the parietal bone of the skull. In this placement, the focus of the focused ultrasound beam will overlap with the left hippocampus and the left posterior cerebral artery (PCA). The right hippocampus will not be targeted and can be used as a control.

A 25 µl bolus of ultrasound contrast agents constituting of microbubbles (mean diameter: 3.0-4.5 µm, concentration: $5.0-8.0 \times 10^8$ bubbles per ml) will be injected into the tail vein 1-4 minutes prior to sonication. Pulsed focused ultrasound (pulse rate: 10 Hz, pulse duration: 20 ms, duty cycle: 20%) will then be applied at 0.64 MPa peak-to-peak in a series of two bursts consisting of 30 s of sonication at a single location (i.e., the hippocampus). Between each burst, a 30-s interval will be allowed for any residual heat between pulses to dissipate. The focused ultrasound sonication procedure can be performed one or more times in each mouse brain.

Following BBB opening, a bipolar recording electrode will be implanted in the hippocampus. Mice will be evaluated to determine which dosages provide prolonged seizure suppression without side effects. An endpoint is at least 8 hours seizure suppression.

Example 6

Prospective Assessment of Efficacy of Ultrasound Enhanced MicroRNA Treatment in Mouse Seizure Model On day one, 50 mice will be injected with kainic acid (KA, 200 ng/nl) in the hippocampus under 2% isoflurane anesthesia. On day 21, AAV 9-pAM/CBA-miR101-1-WPRE-BGHpA (4.66 E+13 genome copies/ml) will be injected in the sclerotic hippocampus (500 nl). In 25 IHKA control mice AAV 9-pAM_CBA-pl-WPRE-BGHpA control vector will be injected. EEG will continuously be recorded and recorded signals will be further processed to quantify the number of seizures.

Prior to AAV 9-pAM/CBA-miR101-1-WPRE-BGHpA administration, ultrasound energy will be applied to the BBB proximate to the hippocampal locus of the modified receptors. Each mouse will be anesthetized using 2% isoflurane and placed prone with its head immobilized by a stereotaxic apparatus that includes a mouse head holder, ear bars, and a gas anesthesia mask. The mouse hair will be removed using an electric trimmer and a depilatory cream. A degassed water-filled container sealed at the bottom with a thin, acoustically and optically transparent plastic wrap will be placed on top of the mouse head. Ultrasound coupling gel will also be used to eliminate any remaining impedance mismatch.

Ultrasound waves will be generated by a single-element spherical segment focused ultrasound transducer (center frequency: 1.525 MHz, focal depth: 90 mm, radius: 30 mm, available, e.g., from Riverside Research Institute, New York, N.Y., USA). A pulse-echo diagnostic transducer (center frequency: 7.5 MHz, focal length: 60 mm) will be aligned through a central, circular hole (radius 11.2 mm) of the focused ultrasound transducer so that the foci of the two transducers fully overlap. A cone filled with degassed and distilled water will be mounted onto the transducer system with the water contained in the cone by an acoustically transparent polyurethane membrane cap. The transducer system will be attached to a computer-controlled, three-dimensional positioning system (e.g., available from Velmex Inc., Lachine, QC, CAN). The focused ultrasound transducer will be connected to a matching circuit and driven by a computer-controlled function generator and a 50-dB power amplifier. The pulse-echo transducer will be driven by a pulser-receiver system connected to a digitizer in a personal computer.

The focused ultrasound transducer will be submerged in the degassed water-filled container with its beam axis perpendicular to the surface of the skull. The focus of the transducer will be positioned inside the mouse brain using, e.g., a grid-positioning method. The beam axis of the transducer will be aligned such that the focal point is placed 3 mm beneath the top of the parietal bone of the skull. In this placement, the focus of the focused ultrasound beam will overlap with the left hippocampus and the left posterior cerebral artery (PCA). The right hippocampus will not be targeted and can be used as a control.

A 25 μl bolus of ultrasound contrast agents constituting of microbubbles (mean diameter: 3.0-4.5 μm, concentration: $5.0-8.0 \times 10^8$ bubbles per ml) will be injected into the tail vein 1-4 minutes prior to sonication. Pulsed focused ultrasound (pulse rate: 10 Hz, pulse duration: 20 ms, duty cycle: 20%) will then be applied at 0.64 MPa peak-to-peak in a series of two bursts consisting of 30 s of sonication at a single location (i.e., the hippocampus). Between each burst, a 30-s interval will be allowed for any residual heat between pulses to dissipate. The focused ultrasound sonication procedure can be performed one or more times in each mouse brain.

Following BBB opening, a bipolar recording electrode will be implanted in the hippocampus. An MRI contrast agent, e.g., gadolinium, will be administered. The contrast agent will be used to determine whether the BBB has been opened by the focused ultrasound treatment. The agent will be observed by use of TI- and T2-weighted MRI scans using a 9.4 T system. The mice will be placed in a plastic tube with a 3.8-cm diameter birdcage coil attached and were inserted vertically into the magnet. Approximately 15 minutes after sonication, but before MRI contrast agent injection, a TI-weighted spin-echo MRI scan will be obtained (TR/TE: 246.1 ms/10 ms; BW: 50,505.1 Hz; matrix size: 256.times.256; FOV: 1.92.times.1.92 cm; slice thickness: 0.6 mm: NEX: 10, 15 and 45). Once the first scan is completed, 0.5 mL of MRI contrast agent gadolinium is administered intraperitoneally via a catheter to depict BBB opening. Intraperitoneal injection allows for the slow uptake of the MRI contrast agent into the bloodstream. After injection of the MRI contrast agent, a series of six alternating T1-weighted and T2-weighted fast spin-echo image scans (TR/TE: 4000 ms/9.2 ms; rapid acquisition with relaxation enhancement: 16; FOV: 1.92.times.1.92 cm; matrix size: 256.times.256; number of slices: 10; slice thickness: 0.6 mm; slice gap: 0.1 mm; NEX: 10, 15 and 45) are taken for each mouse.

Mice will be evaluated to determine which dosages provide prolonged seizure suppression without side effects. An endpoint is at least 8 hours seizure suppression.

It should be understood that the examples and embodiments provided herein are exemplary examples embodiments. Those skilled in the art will envision various modifications of the examples and embodiments that are consistent with the scope of the disclosure herein. Such modifications are intended to be encompassed by the claims.

---

What is claimed is:

1. A method for treating focal cortical dysplasia in a patient in need thereof comprising administering to the patient an effective amount of a liquid pharmaceutical composition comprising a vector including a nucleic acid encoding microRNA-128, pri-miR128 or pre-miR128, wherein said nucleic acid is operably linked to a promoter, and wherein the composition increases the level of microRNA-128, pri-miR128 or pre-miR128 in the patient's brain.

2. The method according to claim 1, wherein after the administering, microRNA-128, pri-miR128 or pre-miR128 is expressed, and expression of microRNA-128, pri-miR128 or pre-miR128, in the patient is associated with reduced symptoms of the focal cortical dysplasia.

3. The method according to claim 1, wherein the nucleic acid encoding microRNA-128, pri-miR128 or pre-miR128, is operably linked to a promoter selected from the group consisting of CAG promoter, CMV promoter, human synapsin 1 gene promoter (hSyn), dynorphin promoter, encephalin promoter and CaMKII promoter.

4. The method according to claim 1, wherein the vector includes a woodchuck post-transcriptional regulatory element (WPRE).

5. The method according to claim 1, wherein the vector includes a bovine growth hormone polyadenylation sequence (BGHpA).

6. The method according to claim 1, wherein the vector includes a fluorescence reporter cassette.

7. The method according to claim 1, wherein the vector is an adeno-associated virus (AAV).

8. The method according to claim 7, wherein the adeno-associated virus is AAV1, AAV2, AAV4, AAV5, AAV7, AVV8, AAV9 or AAVRec3.

9. The method according to claim 1, wherein the vector is a lentivirus.

10. The method according to claim 1, wherein the vector is pAM/CBA-miR128-2-WPRE-BGHpA.

11. The method according to claim 1, wherein the composition is delivered to a target location in the patient's brain.

12. The method according to claim 1, wherein the composition is administered via a route selected from the group consisting of oral, buccal, sublingual, rectal, topical, intranasal, vaginal and parenteral.

13. The method according to claim 1, further comprising applying ultrasound to a target location in the patient's brain to enhance permeability of the patient's blood brain barrier at the target location, wherein the vector is delivered to the target location.

14. The method of claim 1, wherein the composition includes a vector that is a non-viral vector.

15. The method of claim 1, wherein the non-viral vector is a liposome mediated delivery vector.

16. The method according to claim 1, further comprising applying ultrasound to a target location in the patient's brain to enhance permeability of the patient's blood brain barrier at the target location, wherein the composition is delivered to the target location.

* * * * *